US011350933B2

(12) United States Patent
Wellman et al.

(10) Patent No.: US 11,350,933 B2
(45) Date of Patent: Jun. 7, 2022

(54) SURGICAL INSTRUMENT WITH STOWING KNIFE BLADE

(71) Applicant: Intuitive Surgical Operations, Inc., Sunnyvale, CA (US)

(72) Inventors: Ashley Wellman, East Palo Alto, CA (US); William Burbank, Sandy Hook, CT (US); Grant Duque, San Jose, CA (US); Patrick Flanagan, Santa Clara, CA (US)

(73) Assignee: Intuitive Surigical Operations, Inc., Sunnyvale, CA (US)

( * ) Notice: Subject to any disclaimer, the term of this patent is extended or adjusted under 35 U.S.C. 154(b) by 71 days.

(21) Appl. No.: 16/802,304

(22) Filed: Feb. 26, 2020

(65) Prior Publication Data

US 2020/0187939 A1  Jun. 18, 2020

Related U.S. Application Data

(60) Continuation of application No. 15/670,994, filed on Aug. 7, 2017, now Pat. No. 10,610,223, which is a
(Continued)

(51) Int. Cl.
*A61B 17/072* (2006.01)
*A61B 17/068* (2006.01)
(Continued)

(52) U.S. Cl.
CPC ........ *A61B 17/0686* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/115;
(Continued)

(56) References Cited

U.S. PATENT DOCUMENTS

| 4,802,614 A | 2/1989 | Green et al. |
| 5,307,976 A | 5/1994 | Olson et al. |

(Continued)

FOREIGN PATENT DOCUMENTS

| CN | 2751749 Y | 1/2006 |
| CN | 101069649 A | 11/2007 |

(Continued)

OTHER PUBLICATIONS

Extended European Search Report for Application No. 13867527.7, dated Jul. 19, 2016, 8 pages.
(Continued)

*Primary Examiner* — Scott A Smith
(74) *Attorney, Agent, or Firm* — Kilpatrick Townsend & Stockton LLP

(57) ABSTRACT

A surgical instrument includes an elongated shaft and an end effector coupled to the shaft. The end effector includes a first member, a knife member, and a second member. The first member is movable towards a distal end of the end effector. The knife member is pivotally coupled to the first member. The second member is movable towards the distal end of the end effector. The knife member is configured to be in a cutting position during a translation of the first and second members towards the distal end of the end effector. The knife member is rotatable relative to the first member to stow the knife member into a non-cutting position after the translation of the first and second members towards the distal end of the end effector.

21 Claims, 16 Drawing Sheets

Related U.S. Application Data continuation of application No. 14/629,748, filed on Feb. 24, 2015, now Pat. No. 9,757,125, which is a division of application No. 13/662,382, filed on Oct. 26, 2012, now Pat. No. 8,991,678.

(60) Provisional application No. 61/560,225, filed on Nov. 15, 2011.

(51) Int. Cl.

| | |
|---|---|
| A61B 50/13 | (2016.01) |
| A61B 90/00 | (2016.01) |
| A61B 17/115 | (2006.01) |
| A61B 34/00 | (2016.01) |

(52) U.S. Cl.
CPC ............ *A61B 50/13* (2016.02); *A61B 17/068* (2013.01); *A61B 17/115* (2013.01); *A61B 2017/07214* (2013.01); *A61B 2017/07278* (2013.01); *A61B 2017/07285* (2013.01); *A61B 2034/252* (2016.02); *A61B 2090/08021* (2016.02)

(58) Field of Classification Search
CPC ........... A61B 2017/07214; A61B 2017/07271; A61B 2017/07278; A61B 2017/07285; A61B 2017/4805
USPC ..... 227/19, 175.2, 176.1, 180.1; 606/1, 139, 606/143, 167, 219
See application file for complete search history.

(56) References Cited

U.S. PATENT DOCUMENTS

| | | | |
|---|---|---|---|
| 5,433,721 A | 7/1995 | Hooven et al. |
| 5,478,003 A | 12/1995 | Green et al. |
| 5,485,947 A | 1/1996 | Olson et al. |
| 5,489,058 A | 2/1996 | Plyley et al. |
| 5,529,235 A | 6/1996 | Boiarski et al. |
| 5,531,754 A | 7/1996 | Shackelford, Sr. et al. |
| 5,597,107 A | 1/1997 | Knodel et al. |
| 5,632,432 A | 5/1997 | Schulze et al. |
| 5,673,841 A | 10/1997 | Schulze et al. |
| 5,752,644 A | 5/1998 | Bolanos et al. |
| 5,762,255 A | 6/1998 | Chrisman et al. |
| 5,776,156 A | 7/1998 | Shikhman |
| 5,810,240 A | 9/1998 | Robertson |
| 5,816,471 A | 10/1998 | Plyley et al. |
| 5,878,938 A | 3/1999 | Bittner et al. |
| 5,911,353 A | 6/1999 | Bolanos et al. |
| 5,954,259 A | 9/1999 | Viola et al. |
| 6,010,054 A | 1/2000 | Johnson et al. |
| 6,254,621 B1 | 7/2001 | Shackelford et al. |
| 6,716,232 B1 | 4/2004 | Vidal et al. |
| 6,843,403 B2 | 1/2005 | Whitman |
| 7,055,730 B2 | 6/2006 | Ehrenfels et al. |
| 7,134,587 B2 | 11/2006 | Schwemberger et al. |
| 7,278,563 B1 | 10/2007 | Green |
| 7,467,740 B2 | 12/2008 | Shelton, IV et al. |
| 7,604,151 B2 | 10/2009 | Hess et al. |
| 7,641,093 B2 | 1/2010 | Doll et al. |
| 7,726,537 B2 | 6/2010 | Olson et al. |
| 7,896,214 B2 | 3/2011 | Farascioni |
| 7,918,230 B2 | 4/2011 | Whitman et al. |
| 8,225,979 B2 | 7/2012 | Farascioni et al. |
| 8,276,594 B2 | 10/2012 | Shah |
| 8,286,850 B2 | 10/2012 | Viola |
| 8,365,975 B1 | 2/2013 | Manoux et al. |
| 8,657,177 B2 | 2/2014 | Scirica et al. |
| 8,746,533 B2 | 6/2014 | Whitman et al. |
| 8,991,678 B2 | 3/2015 | Wellman et al. |
| 9,498,215 B2 | 11/2016 | Duque et al. |
| 9,757,125 B2 | 9/2017 | Wellman et al. |
| 9,924,941 B2 | 3/2018 | Burbank et al. |
| 10,194,908 B2 | 2/2019 | Duque et al. |
| 10,610,223 B2 | 4/2020 | Wellman et al. |
| 10,912,556 B2 | 2/2021 | Burbank |
| 10,918,387 B2 | 2/2021 | Duque et al. |
| 2003/0055424 A1 | 3/2003 | Ciarrocca |
| 2004/0094597 A1 | 5/2004 | Whitman et al. |
| 2004/0199181 A1 | 10/2004 | Knodel et al. |
| 2004/0215217 A1 | 10/2004 | Banbury et al. |
| 2005/0103819 A1 | 5/2005 | Racenet et al. |
| 2006/0273135 A1 | 12/2006 | Beetel |
| 2007/0023477 A1 | 2/2007 | Whitman et al. |
| 2007/0095877 A1 | 5/2007 | Racenet et al. |
| 2007/0102476 A1 | 5/2007 | Shelton et al. |
| 2007/0123889 A1 | 5/2007 | Malandain et al. |
| 2007/0175950 A1 | 8/2007 | Shelton et al. |
| 2008/0027472 A1 | 1/2008 | Nielsen et al. |
| 2008/0237298 A1 | 10/2008 | Schall et al. |
| 2008/0308601 A1 | 12/2008 | Timm et al. |
| 2009/0302093 A1 | 12/2009 | Kasvikis |
| 2010/0065604 A1 | 3/2010 | Weng |
| 2010/0072257 A1 | 3/2010 | Farascioni |
| 2010/0072258 A1 | 3/2010 | Farascioni et al. |
| 2010/0213238 A1 | 8/2010 | Farascioni et al. |
| 2010/0213240 A1 | 8/2010 | Kostrzewski |
| 2010/0256634 A1 | 10/2010 | Voegele et al. |
| 2010/0292691 A1 | 11/2010 | Brogna |
| 2010/0320252 A1 | 12/2010 | Viola et al. |
| 2011/0068147 A1 | 3/2011 | Racenet et al. |
| 2011/0226837 A1 | 9/2011 | Baxter, III et al. |
| 2011/0315741 A1 | 12/2011 | Nelson et al. |
| 2012/0193393 A1 | 8/2012 | Viola et al. |
| 2012/0209288 A1 | 8/2012 | Robinson |
| 2012/0248167 A1 | 10/2012 | Flanagan et al. |
| 2012/0273551 A1 | 11/2012 | Shelton, IV et al. |
| 2012/0305626 A1 | 12/2012 | Stopek |
| 2012/0310255 A1 | 12/2012 | Brisson et al. |
| 2013/0037597 A1 | 2/2013 | Katre et al. |
| 2013/0098966 A1 | 4/2013 | Kostrzewski et al. |
| 2013/0098968 A1 | 4/2013 | Aranyi et al. |
| 2013/0105552 A1 | 5/2013 | Weir et al. |
| 2013/0240604 A1 | 9/2013 | Knodel |
| 2013/0334284 A1 | 12/2013 | Swayze et al. |
| 2014/0103093 A1 | 4/2014 | Koch, Jr. et al. |
| 2014/0239046 A1 | 8/2014 | Milliman et al. |
| 2015/0320423 A1 | 11/2015 | Aranyi |
| 2017/0333037 A1 | 11/2017 | Wellman et al. |
| 2018/0168572 A1 | 6/2018 | Burbank |
| 2021/0128144 A1 | 5/2021 | Burbank |

FOREIGN PATENT DOCUMENTS

| | | |
|---|---|---|
| CN | 201227300 Y | 4/2009 |
| CN | 101507639 A | 8/2009 |
| CN | 101507643 A | 8/2009 |
| CN | 101801283 A | 8/2010 |
| CN | 101856255 A | 10/2010 |
| CN | 101966093 A | 2/2011 |
| CN | 101999916 A | 4/2011 |
| CN | 102178552 A | 9/2011 |
| CN | 102440814 A | 5/2012 |
| CN | 202446160 U | 9/2012 |
| CN | 102743201 A | 10/2012 |
| EP | 1813201 A1 | 8/2007 |
| EP | 2245993 A2 | 11/2010 |
| EP | 1977701 B1 | 12/2011 |
| EP | 2436319 A2 | 4/2012 |
| JP | H08336540 A | 12/1996 |
| JP | H09262243 A | 10/1997 |
| JP | 2004305741 A | 11/2004 |
| JP | 2005511131 A | 4/2005 |
| JP | 2007216012 A | 8/2007 |
| JP | 2007229448 A | 9/2007 |
| JP | 2009502352 A | 1/2009 |
| JP | 2010240419 A | 10/2010 |
| JP | 2011509715 A | 3/2011 |
| KR | 20070079046 A | 8/2007 |
| KR | 20080031116 A | 4/2008 |
| WO | WO-2006124388 A1 | 11/2006 |
| WO | WO-2011060042 A1 | 5/2011 |

(56) References Cited

FOREIGN PATENT DOCUMENTS

| WO | WO-2012040984 A1 | 4/2012 |
| WO | WO-2012112249 A1 | 8/2012 |
| WO | WO-2013063523 A1 | 5/2013 |
| WO | WO-2013063525 A1 | 5/2013 |
| WO | WO-2013074272 A2 | 5/2013 |

OTHER PUBLICATIONS

Extended European Search Report for Application No. 19158752.6 dated Jun. 25, 2019, 13 pages.
Extended European Search Report for Application No. 19164999.5 dated Jul. 24, 2019, 10 pages.
Extended European Search Report for Application No. EP12850096.4, dated Jun. 25, 2015, 8 pages.
Extended European Search Report for Application No. EP20120844202, dated Jun. 12, 2015, 10 pages.
International Search Report and Written Opinion for Application No. PCT/US13/78549, dated Apr. 16, 2014, 12 pages.
International Search Report and Written Opinion for Application No. PCT/US2012/062302 dated Feb. 26, 2013, 10 pages.
International Search Report and Written Opinion for Application No. PCT/US2012/062305, dated Feb. 26, 2013, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

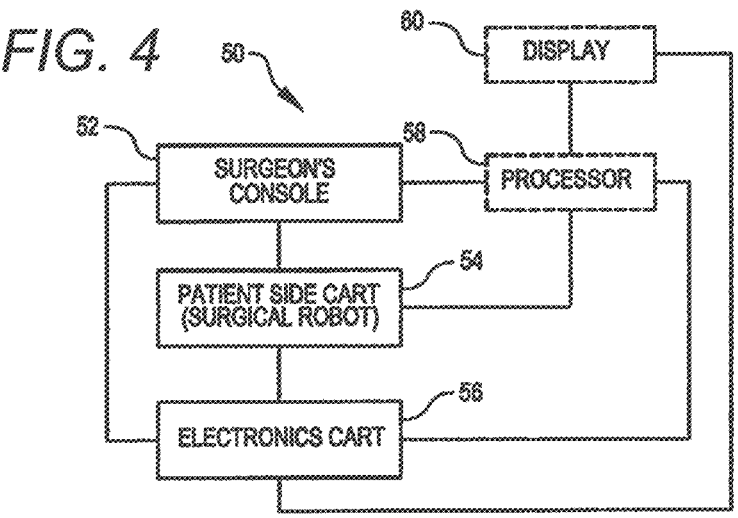
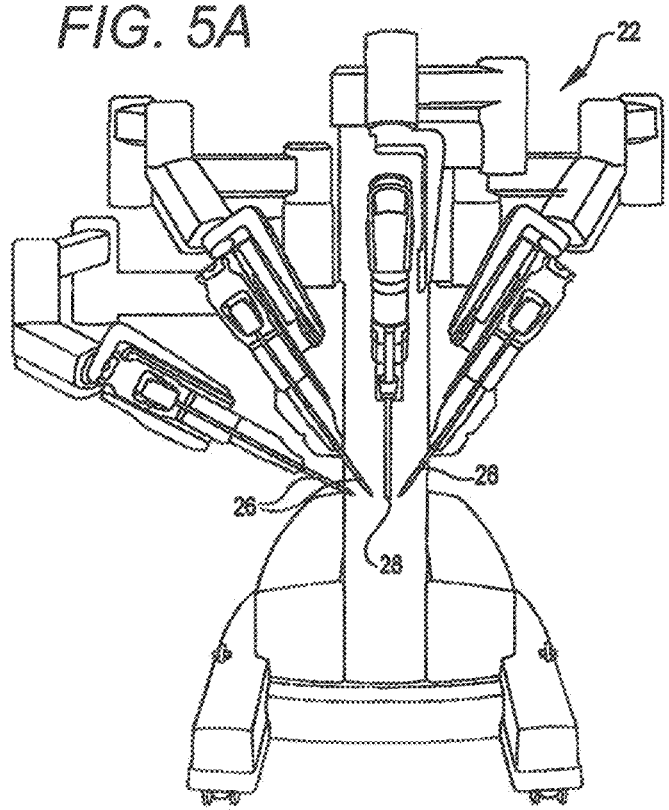

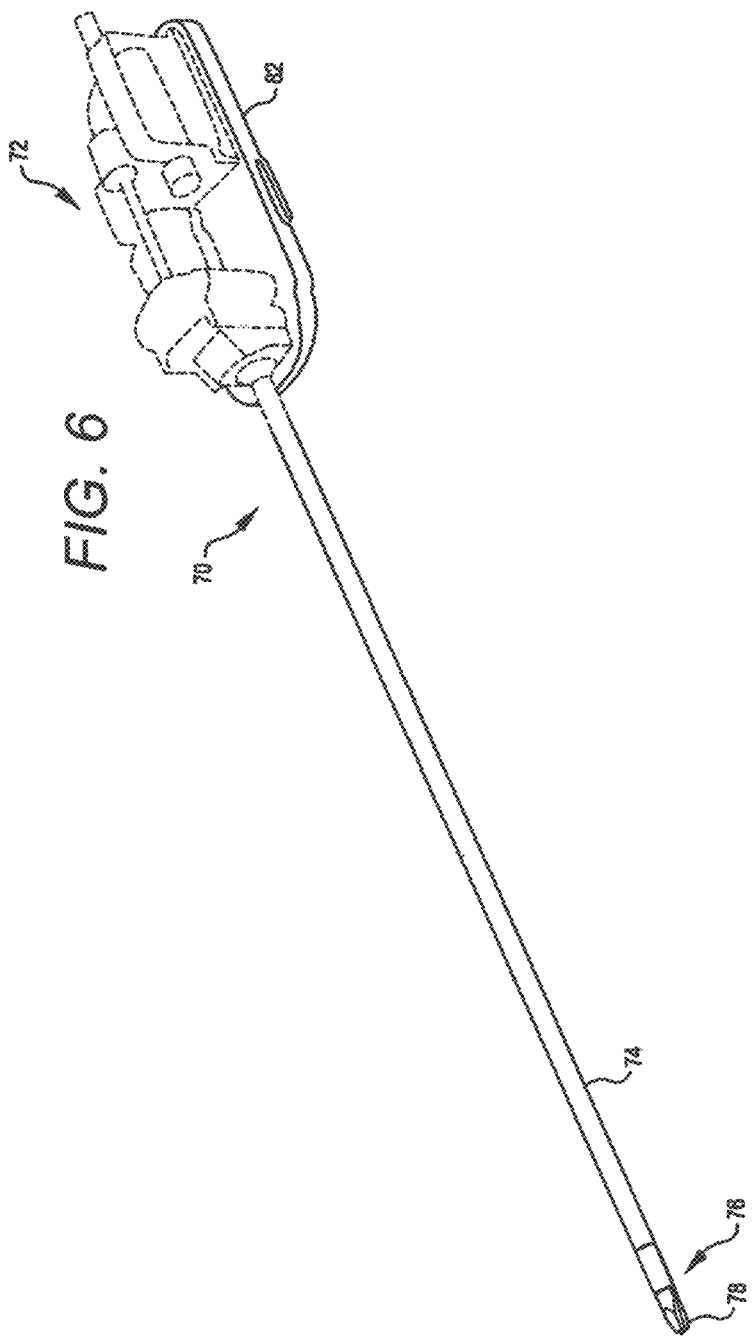

SURGICAL INSTRUMENT WITH STOWING KNIFE BLADE

CROSS REFERENCE TO RELATED APPLICATIONS

The present application is a Continuation of U.S. application Ser. No. 15/670,994 filed Aug. 7, 2017 (now U.S. Pat. No. 10,610,223); which is a Continuation of U.S. application Ser. No. 14/629,748 filed Feb. 24, 2015 (now U.S. Pat. No. 9,757,125); which is a Divisional of U.S. application Ser. No. 13/662,382 filed Oct. 26, 2012 (now U.S. Pat. No. 8,991,678); which claims the benefit of U.S. Provisional Application No. 61/560,225 filed Nov. 15, 2011; the full disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastrointestinal tract. Many known surgical clamping and cutting devices, including known surgical staplers, have opposing jaws that clamp tissue and an articulated knife to cut the clamped tissue.

Surgical clamping and cutting instruments are often deployed into restrictive body cavities (e.g., through a cannula to inside the pelvis). Accordingly, it is desirable for the surgical clamping and cutting instrument to be both compact and maneuverable for best access to and visibility of the surgical site. Known surgical clamping and cutting instruments, however, may fail to be both compact and maneuverable. For example, known surgical staplers may lack maneuverability with respect to multiple degrees of freedom (e.g., Roll, Pitch, and Yaw) and associated desired ranges of motion. Typically, known surgical staplers have a smaller range of Pitch motion than desirable and no Yaw motion.

Additionally, surgical clamping and cutting instruments can sometimes fail to fully actuate (e.g., due to a hard obstacle blocking the knife path), potentially leaving a knife blade exposed. In such an event, it is desirable that the knife blade not be in a position that may represent a hazard with respect to removal of the surgical instrument from the surgical site. Known surgical clamping and cutting instruments, however, may fail to avoid the potential knife hazard and at the same time be compact and maneuverable.

Thus, there is believed to be a need for improved surgical clamping and cutting instruments and related methods. Such surgical clamping and cutting instruments should be compact and maneuverable, and employ a knife that does not represent a hazard with respect to removal of the surgical instrument from the surgical site when the surgical instrument fails to fully actuate.

BRIEF SUMMARY

Improved surgical clamping and cutting instruments (e.g., surgical staplers, and electrosurgical vessel sealing devices) and related methods are disclosed. Surgical clamping and cutting instruments described herein employ a proximal-to-distal knife movement, thereby orienting the knife to reduce the likelihood of unintentionally cutting tissue while removing the surgical instrument from the surgical site in the event that the surgical instrument fails to fully actuate. The surgical instruments described herein include first and second moving members that are moved toward the distal end at the same rate through a first distance to cut tissue and subsequently move relative to each other to facilitate stowing of the knife.

Thus, in one aspect, a method of articulating a knife in a surgical instrument is disclosed. The surgical instrument has a proximal end and a distal end. The method includes pivotally supporting the knife from a first member. The knife is configured to cut when the knife is moved toward the distal end. A rotation of the knife relative to the first member is blocked with the second member while moving the first member and a second member toward the distal end at the same rate. After moving the first and second members toward the distal end at the same rate, relative movement between the first and second members is generated to accomplish at least one of permitting rotation of the knife or inducing rotation of the knife.

In many embodiments, a lead screw is used to actuate the first and second members. For example, moving the first and second members towards the distal end at the same rate can include rotating a lead screw having a threaded portion operatively coupled with at least one of the first member or the second member. Generating relative movement between the first and second members can include rotating a lead screw having a threaded portion and a non-threaded portion. The threaded portion can be operatively coupled with one of the first and second members and the non-threaded portion can interface with the other of the first and second members such that rotation of the lead screw generates the relative motion between the first and second members.

Any suitable relative movement between the first and second members can be used. For example, generating relative movement between the first and second members can include moving the either one of the first member or the second member toward the distal end while preventing the other one of the first and second members from moving toward the distal end to reposition the second member relative to the first member to not block the rotation of the knife. As another example, generating relative movement between the first and second members can include moving the either one of the first member or the second member toward the proximal end while preventing the other one of the first and second members from moving toward the proximal end to reposition the second member relative to the first member to not block the rotation of the knife.

In many embodiments, the relative movement between the first and second members induces rotation of the knife relative to the first member. For example, the knife can include external gear teeth that mate with external gear teeth coupled with the second member so that the relative movement between the first and second members causes movement of the second member gear teeth relative to the knife gear teeth and corresponding rotation of the knife relative to the first member.

The knife can engage one or more features to selectively cause the knife to rotate into a desired position. For example, the method can include engaging the knife with a kick-down feature to cause the knife to rotate relative to the first member to stow a cutting edge of the knife below an upper surface of the housing. As another example, the method can include engaging the knife with a kick-down feature coupled to the second member thereby causing the knife to rotate relative to the first member to stow a cutting edge of the knife below the upper surface of the housing. As an additional example, the method can include engaging the knife with a kick-up feature to cause the knife to rotate into a cutting position during the movement of the first and second members towards the distal end at the same rate.

The method can further include additional acts performed using the surgical instrument. For example, the method can include deploying staples during the movement of the first and second members toward the distal end at the same rate.

In another aspect, a surgical instrument is disclosed. The surgical instrument includes an elongated shaft having a shaft distal end and a shaft proximal end, an end effector coupled to the shaft distal end and including two opposed jaws, a housing included in one of the jaws, a first member mounted in the housing and movable toward the housing distal end, a knife, and a second member. The second member is configured to move with the first member toward the housing distal end through a first distance. Relative movement between the first and second members occurs after the first and second members move through the first distance. The housing includes a housing proximal end, a housing distal end, an upper surface extending between the housing proximal and distal ends, a central cavity extending between the housing proximal and distal ends, and a longitudinal slot extending through the upper surface. The knife is pivotally coupled with the first member. The knife has a cutting edge configured to cut when the first member is moved toward the housing distal end. The cutting edge extends above the housing upper surface for at least a portion of the distal movement of the first member. The second member blocks a rotation of the knife relative to the first member while moving with the first member at the same rate toward the housing distal end and at least one of permits rotation of the knife after a relative movement between the first and second members or induces rotation of the knife during a relative movement between the first and second members.

In many embodiments, the surgical instrument includes a lead screw coupled with the housing for rotation relative to the housing. The lead screw is operatively coupled with at least one of the first member or the second member to drive the coupled member along at least a portion of the lead screw in response to rotation of the lead screw. For example, the lead screw can have a threaded portion and a non-threaded portion disposed distally of the threaded portion. Both the first and second members can be driven along the lead screw when the second member moves with the first member toward the housing distal end at the same rate. To generate the relative movement between the first and second members, one of the first and second members can be interfaced with the non-threaded portion and the other one of the first and second members can be interfaced with the threaded portion.

The surgical instrument can employ any suitable relative movement between the first and second members. For example, the first member or the second member can move toward the housing distal end when the second member moves relative to the first member. As another example, the first member or the second member can move toward the housing proximal end when the second member moves relative to the first member.

In many embodiments of the surgical instrument, the relative movement between the first and second members induces rotation of the knife relative to the first member. For example, the knife can include gear teeth that mate with gear teeth coupled with the second member so that the relative movement between the first and second members causes movement of the second member gear teeth relative to the knife gear teeth and corresponding rotation of the knife relative to the first member.

In many embodiments of the surgical instrument, the second member moves along with the first member until prevented from doing so. For example, the second member can be prevented from moving toward the housing distal end during a movement of the first member toward the housing distal end to reposition the second member to not block the rotation of the knife. In many embodiments, the second member is slidably mounted to the first member to move with the first member along the first distance and to not move toward the distal end during a movement of the first member toward the distal end.

The surgical instrument can include one or more features to selectively rotate the knife into a desired position. For example, the surgical instrument can include a kick-down feature coupled with the housing to cause the knife to rotate relative to the first member to stow the cutting edge of the knife below an upper surface of the housing. As another example, the surgical instrument can include a kick-down feature coupled to the second member to cause the knife to rotate relative to the first member to stow the cutting edge of the knife below an upper surface of the housing during the relative motion between the first and second members. As an additional example, the surgical instrument can include a kick-up feature coupled with the housing to cause the knife to rotate into a cutting position during the movement of the first and second members towards the distal end at the same rate.

The surgical instrument can include additional features providing additional functionality. For example, the housing can include a plurality of staple openings extending between the upper surface and the central cavity. A plurality of staples can be disposed in the staple openings, each of the staples being deployed during a movement of the first and second members toward the housing distal end at the same rate.

In another aspect, a demountably attachable cartridge of a surgical instrument is disclosed. The cartridge includes a housing demountably attachable to an end effector of the surgical instrument, a first member mounted in the housing and movable toward a distal end of the housing, a knife, and a second member. The second member is operable to move with the first member toward the distal end through a first distance. Relative movement between the first and second members occurs after the first and second members move through the first distance. The housing includes a proximal end, a distal end, an upper surface extending between the proximal and distal ends, a central cavity extending between the proximal and distal ends, and a longitudinal slot extending through the upper surface. The knife is pivotally coupled with the first member or the second member. The knife has a cutting edge configured to cut when moved toward the distal end. The cutting edge extends through the longitudinal slot for at least a portion of the movement of the first member along the lead screw. The second member blocks a rotation of the knife relative to the first member while moving with the first member. The second member at least one of permits rotation of the knife or induces rotation of the knife after a relative movement between the first and second members.

In many embodiments, the cartridge includes a lead screw coupled with the housing for rotation relative to the housing. The lead screw is operatively coupled with at least one of the first member or the second member to drive the coupled member along at least a portion of the lead screw in response to rotation of the lead screw. For example, the lead screw can have a threaded portion and a non-threaded portion disposed distally of the threaded portion. Both the first and second members can be driven along the lead screw when the second member moves with the first member toward the housing distal end at the same rate. To generate the relative movement between the first and second members, one of the first and second members can be interfaced with the non-threaded portion and the other one of the first and second members can be interfaced with the threaded portion.

In many embodiments of the cartridge, the lead screw has a threaded portion and a non-threaded portion disposed toward the distal end relative to the threaded portion. Both the first and second members are driven along the threaded portion when the second member moves with the first member toward the distal end at the same rate. One of the first and second members can interface with the threaded portion and the other one of the first and second members can interface with the non-threaded portion to generate the relative movement between the first and second members in response to a rotation of the lead screw.

The cartridge can employ any suitable relative movement between the first and second members. For example, the first member or the second member can move toward the housing distal end when the second member moves relative to the first member. As another example, the first member or the second member can move toward the housing proximal end when the second member moves relative to the first member.

In many embodiments of the cartridge, the relative movement between the first and second members induces rotation of the knife relative to the first member. For example, the knife can include gear teeth that mate with gear teeth coupled with the second member so that the relative movement between the first and second members causes movement of the second member gear teeth relative to the knife gear teeth and corresponding rotation of the knife relative to the first member.

In many embodiments of the cartridge, the second member moves along with the first member until prevented from doing so. For example, the second member can be prevented from moving toward the distal end during a movement of the first member toward the distal end to reposition the second member to not block the rotation of the knife. In many embodiments, the second member is slidably mounted to the first member to move with the first member along the first distance and to not move toward the distal end during a movement of the first member toward the distal end.

The cartridge can include one or more features to selectively rotate the knife into a desired position. For example, the cartridge can include a kick-down feature coupled with the housing to cause the knife to rotate relative to the first member to stow a cutting edge of the knife below an upper surface of the housing. As another example, the cartridge can include a kick-down feature coupled to the second member to cause the knife to rotate during a relative movement between the first and second members to stow a cutting edge of the knife below the upper surface of the housing. As an additional example, the cartridge can include a kick-up feature coupled with the housing to cause the knife to rotate into a cutting position during the movement of the second member with the first member toward the distal end at the same rate.

The cartridge can include additional features providing additional functionality. For example, the housing can include a plurality of staple openings extending between the upper surface and the central cavity. A plurality of staples can be disposed in the staple openings, each of the staples being deployed during a movement of the first and second members toward the distal end at the same rate.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 4 diagrammatically illustrates a robotic surgery system, in accordance with many embodiments.

FIG. 5A is a front view of a patient side cart (surgical robot) of a robotic surgery system, in accordance with many embodiments.

FIG. 6 is a perspective view of a robotic surgery tool that includes an end effector having opposed clamping jaws, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
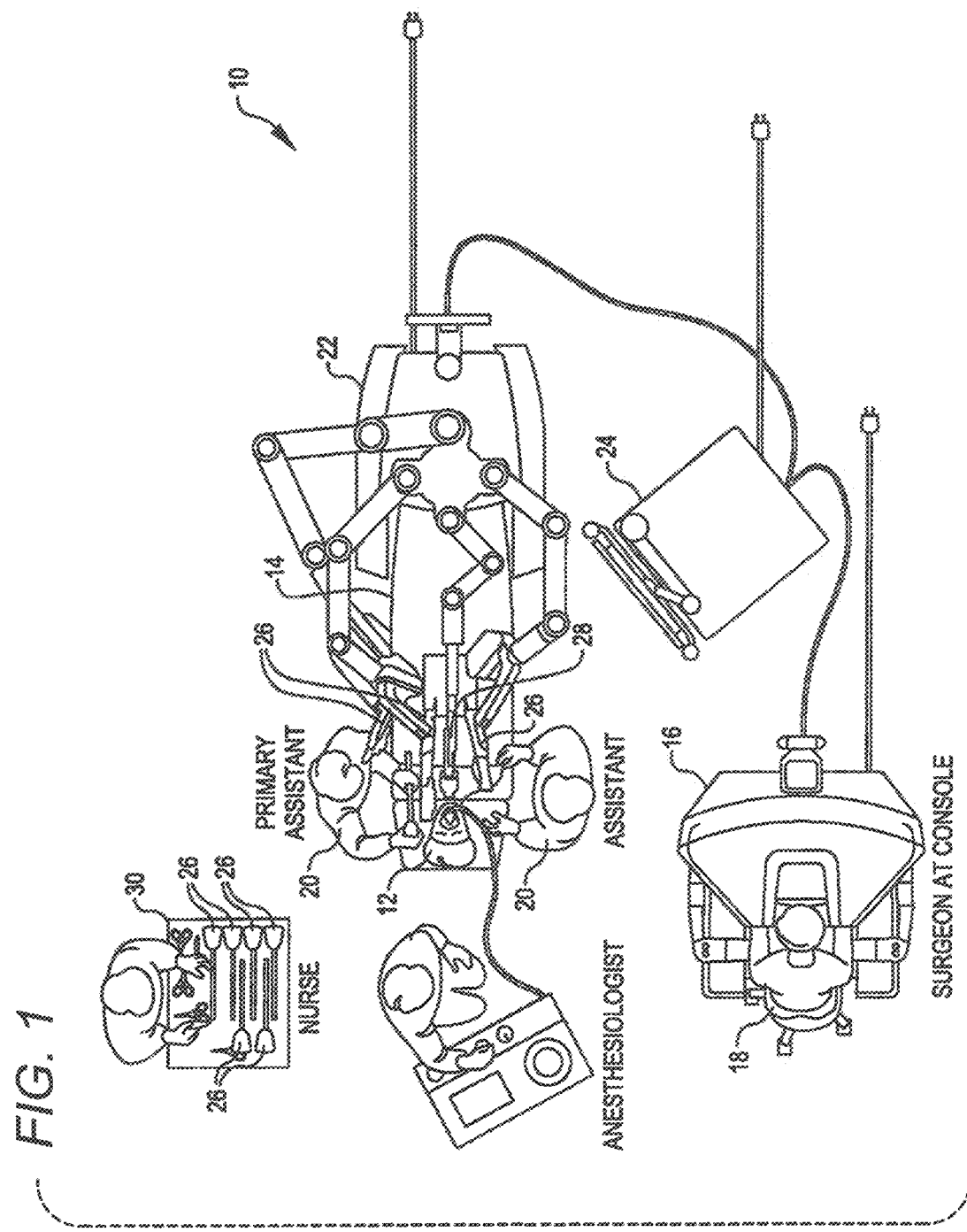
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
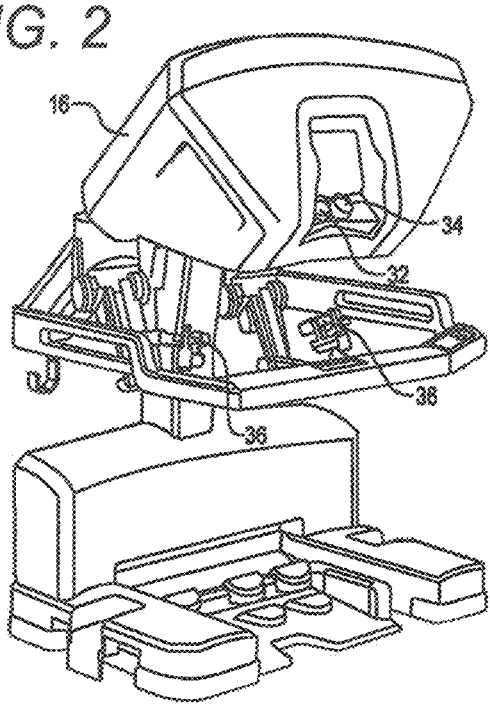
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
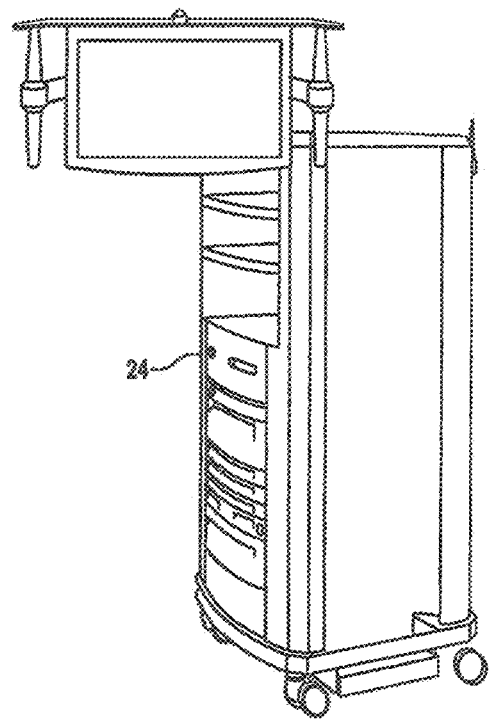
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5B:
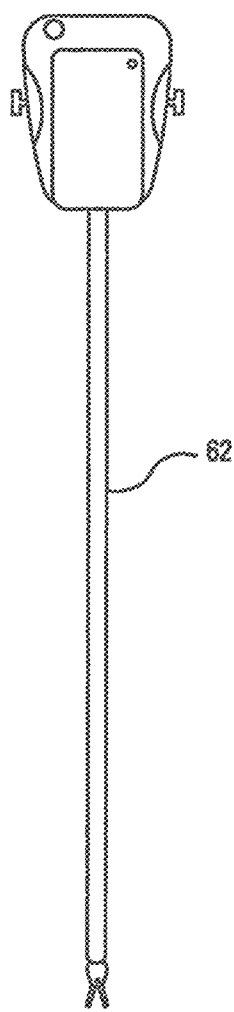
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Tissue Gripping End Effectors

FIG. 6 shows a surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Linear Stapling and Cutting Surgical Instruments

Figure 7:
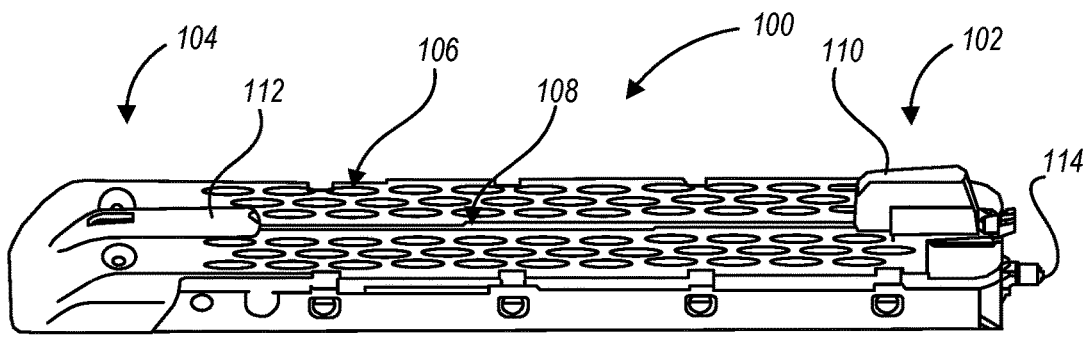
FIG. 7 is a perspective view of a demountably attachable cartridge of a linear stapling and cutting surgical instrument, in accordance with many embodiments.
Figure 8:
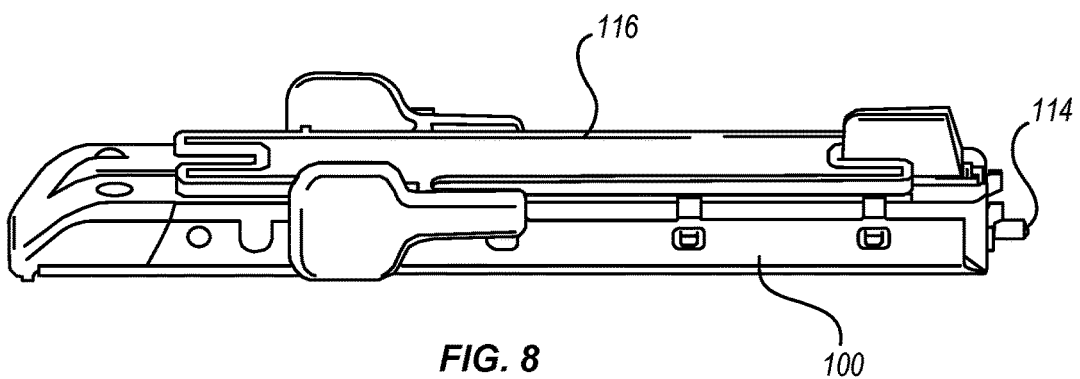
FIG. 8 is a perspective view of the cartridge of FIG. 7 and an attached staple retainer, in accordance with many embodiments.

FIG. 7 shows a demountably attachable cartridge 100 of a linear stapling and cutting surgical instrument, in accordance with many embodiments. The cartridge 100 is configured to removably attach to a jaw of an end effector. The cartridge has a proximal end 102 that is attached to the jaw of the end effector and a distal end 104 disposed at a corresponding distal end of the jaw of the end effector. The cartridge 100 includes six rows of staple openings 106, a longitudinal slot 108, a proximal knife garage 110, a distal knife garage 112, and a rotational input 114. In many embodiments, a staple is disposed in each of the staple openings for deployment there from. The longitudinal slot 108 accommodates a cutting blade of a knife member (not shown) extending there from as the knife member is moved from the proximal knife garage 110 to the distal knife garage 112. In operation, the staples are deployed starting at the cartridge proximal end 102 and proceeding to the cartridge distal end 104. The cutting blade is moved to trail the stapling of the tissue to ensure that only fully stapled tissue is cut. FIG. 8 shows the cartridge 100 with an attached staple retainer 116, which is removed prior to using the cartridge 100.

Figure 9:
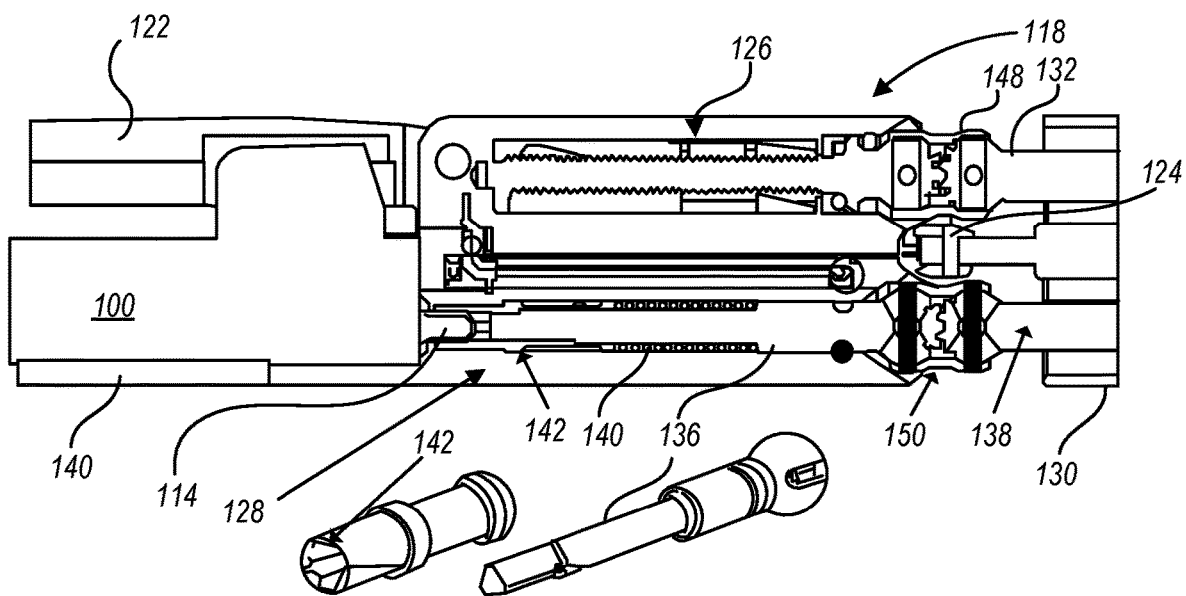
FIG. 9 is a cross-sectional view showing attachment details between the cartridge of FIG. 7 and an end effector assembly, in accordance with many embodiments.

FIG. 9 is a cross-sectional view showing details of the attachment of the cartridge 100 to an end effector 118, in accordance with many embodiments. The end effector 118 includes a lower jaw 120, an upper jaw 122, a two degree of freedom wrist 124, a rotationally-driven clamping mechanism 126, and a spring loaded coupling 128. The lower jaw 120 is configured to accommodate and support the cartridge 100, as well as position the cartridge 100 relative to the spring loaded coupling 128. The upper jaw 122 is pivotally coupled with the lower jaw 120 to articulate relative to the lower jaw 120 to clamp tissue. The upper jaw 122 includes staple forming recesses configured and positioned relative to the staple openings 106 to form the staples into a "B" shape upon deployment of the staples.

The two degree of freedom wrist 124 provides for attachment of the end effector 118 to an elongated instrument shaft 130 for articulation of the end effector 118 about two orthogonal axes relative to the instrument shaft 130. Details of a suitable two degree of freedom wrist that can be used are disclosed in U.S. application Ser. No. 12/945,748 filed Nov. 12, 2010, entitled "SURGICAL TOOL WITH A TWO DEGREE OF FREEDOM WRIST" (now issued as U.S. Pat. No. 8,852,174), the full disclosure of which is hereby incorporated herein by reference.

The rotationally-driven clamping mechanism 126 actuates the upper jaw 122 relative to the lower jaw 120 to securely clamp tissue between the upper and lower jaws. The clamping mechanism 126 is rotationally driven by a first drive shaft 132 disposed internal to the instrument shaft 130. Details of a suitable rotationally-driven clamping mechanism that can be used are disclosed in U.S. application Ser. No. 12/945,541 filed Nov. 12, 2010, entitled "END EFFECTOR WITH REDUNDANT CLOSING MECHANISMS"

(now issued as U.S. Pat. No. 8,876,857) the full disclosure of which is hereby incorporated herein by reference.

The spring-loaded coupling 128 rotationally couples the rotational input 114 of the cartridge 100 with an extension shaft 136, which is driven by a second drive shaft 138 disposed internal to the instrument shaft 130. The spring-loaded coupling 128 includes a coil spring 140 and a coupling fitting 142. In the embodiment shown, the coupling fitting 142 employs a three-lobe spline receptacle that interfaces with three-sided external surfaces of the rotational input 114 and of the extension shaft 136. The spring-loaded coupling 142 accommodates angular misalignment of the three-lobe spline that might occur when the cartridge 100 is installed into the end effector 118. The spring-loaded coupling 142 fully engages the three-lobe spline when rotated into angular alignment. Rotation of the rotational input 114 is used to translate a drive member of the cartridge 100. The resulting motion of the drive member is used to deploy the staples and to distally advance a knife member to cut the clamped tissue down the center of the rows of deployed staples.

The end effector 118 includes a first universal joint assembly 148 and a second universal joint assembly 150. The first universal joint assembly 148 rotationally couples the clamping mechanism 126 to the first drive shaft 132. The second universal joint assembly 150 rotationally couples the extension shaft 136 to the second drive shaft 138. Each of the first and second universal joint assemblies 148, 150 is configured to transmit torque through a range of angles suitable to the range of Pitch and Yaw of the end effector 118 relative to the instrument shaft 130. Details of a suitable universal joint assembly that can be used are disclosed in U.S. application Ser. No. 12/945,740 filed Nov. 12, 2010, entitled "DOUBLE UNIVERSAL JOINT," the full disclosure of which is hereby incorporated herein by reference.

The first and second drive shafts 132, 138 are disposed offset to the centerline of the instrument shaft 130, which may be independently rotated. Details of a suitable drive mechanism that can be used to actuate the first and second drive shafts 132, 138 are disclosed in U.S. application Ser. No. 12/945,461 filed Nov. 12, 2010, entitled "MOTOR INTERFACE FOR PARALLEL DRIVE SHAFTS WITHIN AN INDEPENDENTLY ROTATING MEMBER," (now issued as U.S. Pat. No. 8,640,788) the full disclosure of which is hereby incorporated herein by reference.

Figure 10:
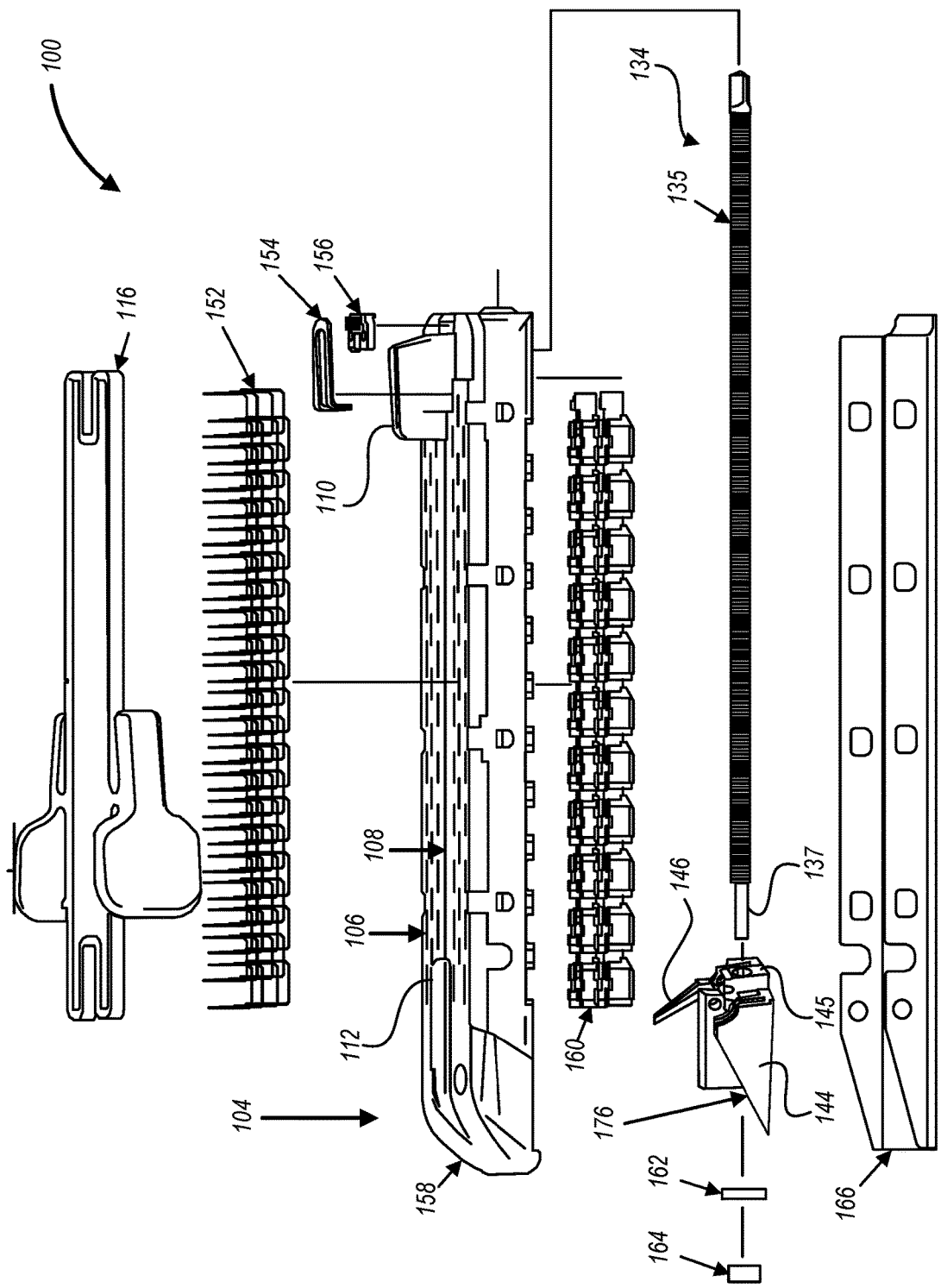
FIG. 10 is an exploded perspective view illustrating components of the cartridge of the cartridge of FIG. 7.

FIG. 10 is an exploded perspective view illustrating components of the cartridge 100. The illustrated components include the retainer 116, 66 staples 152, a printed circuit assembly (PCA) spring 154, a PCA 156, a cartridge body 158, 22 staple pushers 160, a first drive member 144, a second drive member 145, a knife 146, a lead screw 134, a thrust washer 162, a lead screw nut 164, and a cover 166. The cartridge body 158 has the 66 staple openings 106 arranged in 6 rows, with 3 rows of the staple openings 106 being disposed on each side of the longitudinal slot 108. The retainer 116 is removably attachable to the cartridge 100 and covers the staple openings 106 to retain the staples 152 prior to use of the cartridge 100. The staple pushers 160 interface with the staples 152 and slidingly interface with the cartridge body 158. The lead screw 134 has a threaded portion 135 and a non-threaded portion 137 disposed toward the distal end 104 relative to the threaded portion 137. Motion of the first drive member 144 along the threaded portion 135 of the lead screw 134 results in engagement of the staple pushers 160 by distally-facing ramp surfaces 176 of the first drive member 144 to drive the staple pushers 160 up relative to the cartridge body 158 to deploy the staples 152 as the first drive member 144 moves towards the distal end 104. The knife 146 is pivotally supported from the first drive member 144. The knife 146 includes external gear teeth that interface with external gear teeth of the second drive member 145. The cover 166 is attached to the cartridge body 158.

Figure 11A:
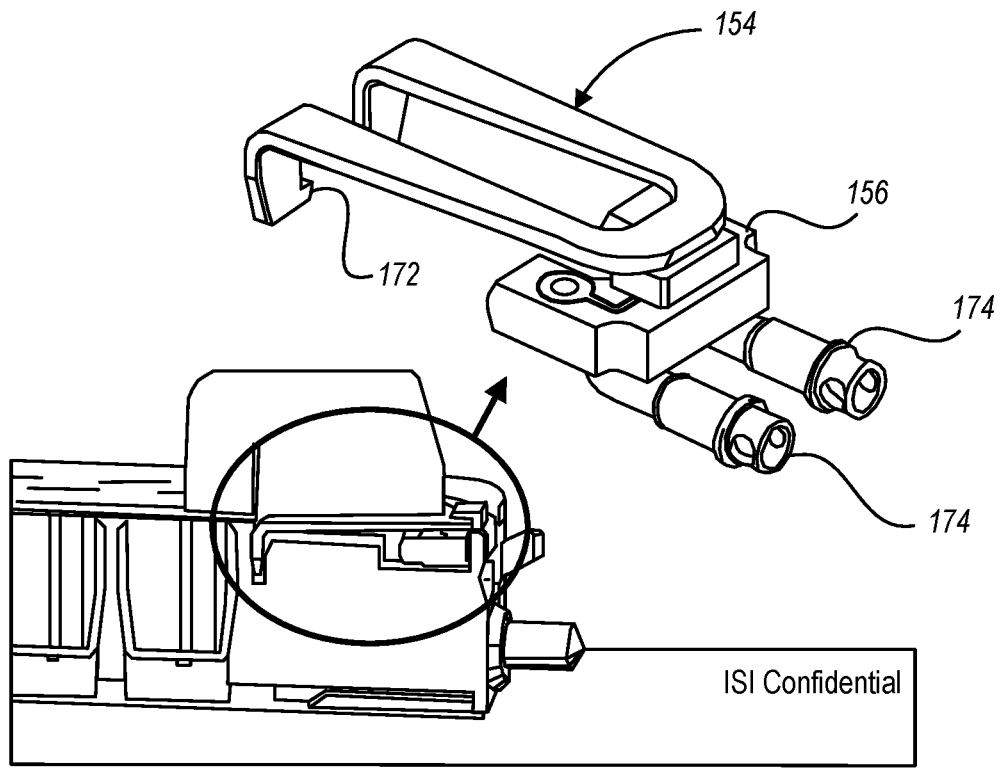
FIGS. 11A and 11B are perspective views illustrating a printed circuit assembly of the cartridge of FIG. 7.
Figure 11B:
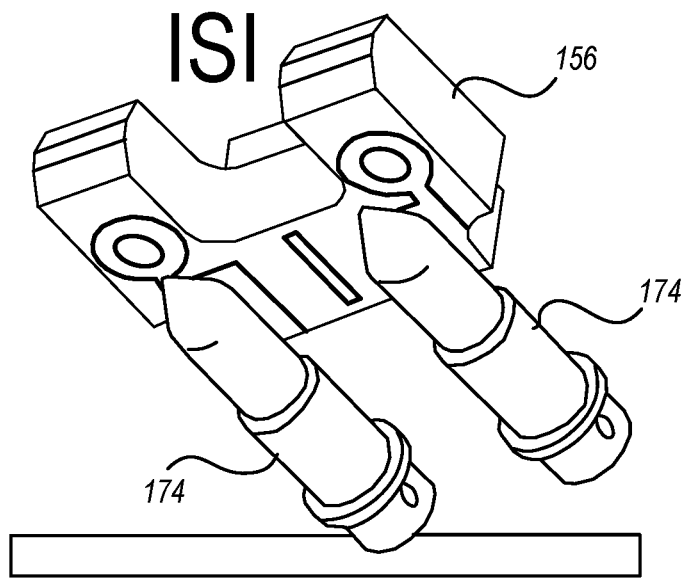

FIGS. 11A and 11B further illustrate the PCA 156 and the PCA spring 154. The PCA spring 154 interfaces with the cartridge body 158 and retains the PCA 156. The PCA spring 154 includes PCA spring hooks 172, which latch onto the cartridge body 158 to retain the PCA spring 154. When the cartridge 100 is attached to the end effector 118, instrument pins 174 of the end effector 118 slide beneath and lift the PCA 156, thereby electrically connecting the PCA 156 with the instrument pins 174 and allowing for the use of increased associated tolerances. This arrangement however is not critical, as long as the instrument pins 174 make suitable contact with the PCA 156. Accordingly, in some embodiments, the PCA 156 can be turned on edge such that the shown chip is out of the load path. The PCA 156 can be used to electronically store identification, configuration, and/or use information associated with the cartridge 100.

The cartridge 100 can be assembled using the following assembly sequence. First, with the cartridge body 158 in a "bottom up" orientation, the staple pushers 160 are installed into the staple openings 106. Next, the first drive member 144, the knife 145 pivotally supported from the first drive member 144, the second drive member 145, the thrust washer 162, and the lead screw nut 164 are installed onto the lead screw 134 and the lead screw nut 164 is laser welded flush to the end of the lead screw 134. The resulting lead screw assembly is then installed into the cartridge body 158 with the first drive member 144 and the second drive member 145 positioned at the proximal end of the lead screw 134 with suitable positioning of the second drive member 145 relative to the first drive member 144 to place the knife 145 in a suitable orientation relative to the first drive member 144 to cut tissue as the first drive member 144 is advanced distally and consistent with stowing of the knife 146 near the end of the travel of the knife 145 toward the distal end of the cartridge body 158. The resulting assembly can then be lubricated, for example, by immersing the resulting assembly into a lubricant. Next, the cover 166 is installed onto the cartridge body 158. Next, the assembly is flipped to a "top up" orientation and the PCA 156 is installed. Next, the PCA spring 154 is pushed onto the cartridge body 158 until the PCA spring hooks 172 latch. Next, the staples 152 are installed into the staple openings 106 and the retainer 116 is then installed. Finally, data is installed into the PCA 156.

Figure 12A:
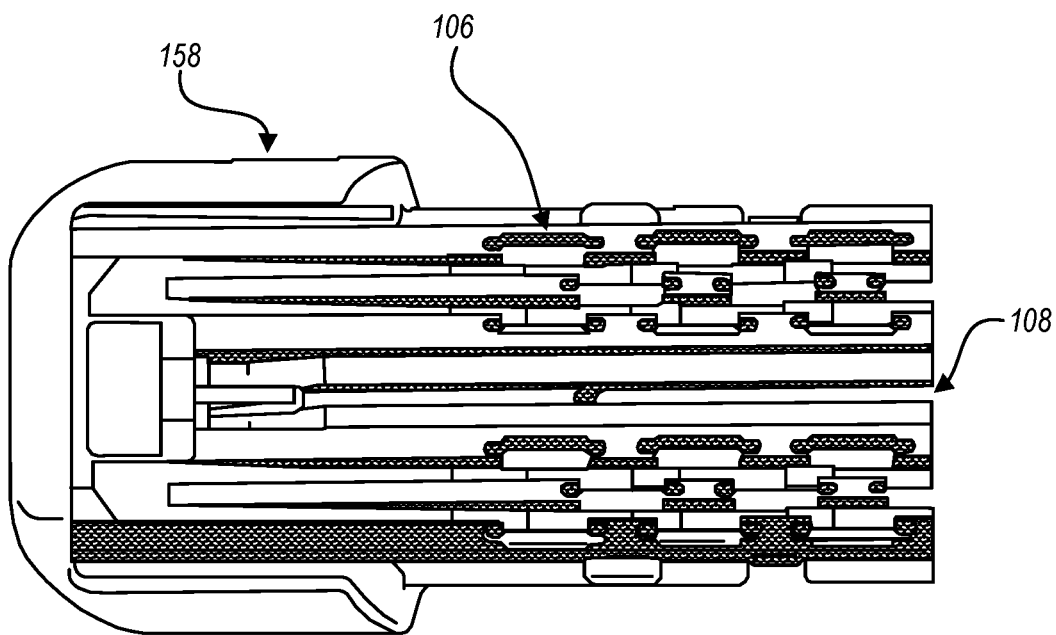
FIG. 12A shows a distal end of a housing of the cartridge of FIG. 7.
Figure 12B:
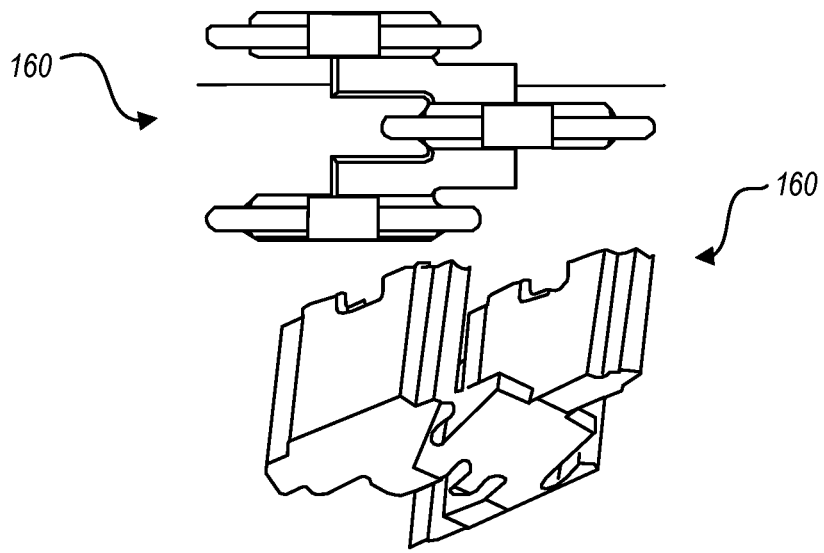
FIG. 12B includes perspective views of a staple pusher of the cartridge of FIG. 7.

FIG. 12A shows a distal end of the cartridge body 158. FIG. 12B shows a top view and a perspective view of one of the staple pushers 160. As illustrated, the staple openings 106 and the staple pushers 160 have complementary shapes such that each of the staple pushers 160 is accommodated within one of the staple openings 106 for translation within the staple opening 106 in response to being driven by the drive member 144 as the drive member 144 is translated toward the cartridge distal end 104.

Figure 13A:
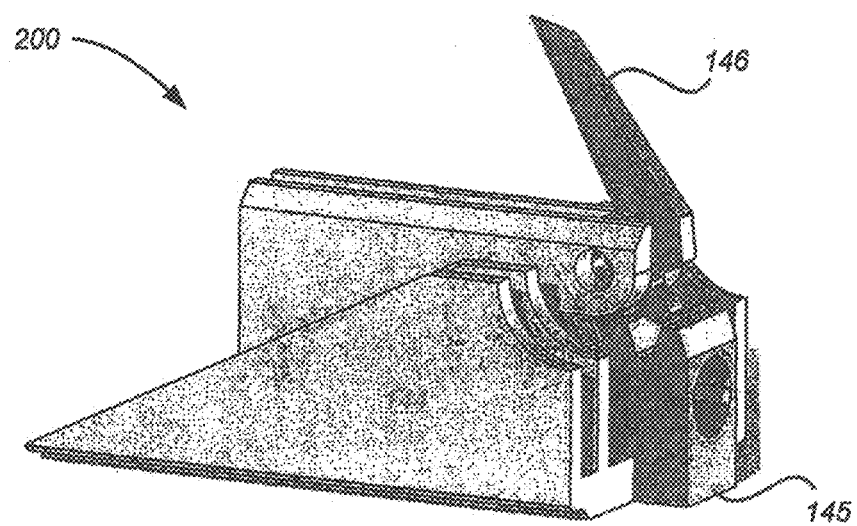
FIG. 13A is a perspective view illustrating knife articulation and staple deployment related components of the cartridge of FIG. 7.
Figure 13B:
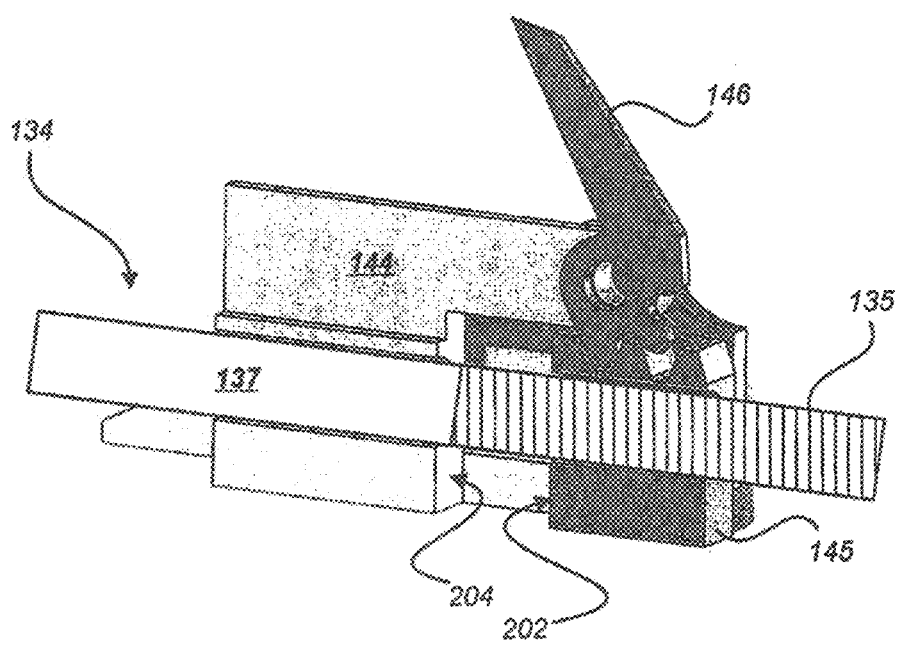
FIG. 13B is a perspective cross-sectional view further illustrating knife articulation and staple deployment related components of the cartridge of FIG. 7.

FIG. 13A shows an assembly 200 of the cartridge 100 that includes the first drive member 144, the knife 146 pivotally supported from the first drive member 144 (pivot pin not shown), and the second drive member 145. FIG. 13B shows the assembly coupled with the lead screw 134. Each of the first drive member 144 and the second drive member 145 include internal threads that operatively couple with the threaded portion 135 of the lead screw 134 for simultaneous translation along the lead screw 134 in response to rotation of the lead screw 134. As the first and second drive members 144, 145 translate along the threaded portion 135, the first and second drive members 144, 145 maintain fixed relative positioning thereby blocking rotation of the knife 146 relative to the first drive member 144 via the gearing interface between the second drive member 145 and the knife 146. Near the end of the articulation of the knife 146, the first drive member 144 is driven onto the non-threaded portion 137 of the lead screw 134. Thereafter, continued rotation of the lead screw 134 results in continued distal movement of the second drive member 145 relative to the cartridge body 158 with no further distal movement of the first drive member 144 relative to the cartridge body 158. The resulting relative distal movement of the second drive member 145 relative to the first drive member 144 rotates the knife 146 relative to the first drive member 144 to stow the knife 146, for example, into the longitudinal slot 108. The assembly 200 can be configured such that a distal surface 202 of the second drive member 145 contacts a proximal surface 204 of the first drive member 144 to end the rotation of the knife 146 relative to the first drive member 144. Thereafter, continued distal movement of the second drive member 145 along the threaded portion 135 can be used to drive the assembly 200 distally, for example, into the distal garage 112 of the cartridge 158.

In the embodiment shown, once the first drive member 144 is driven onto the non-threaded portion 137, continued distal movement of the second drive member 145 along the lead screw 134 is used to stow the knife 146. Alternatively, after the first drive member 144 has been driven onto the non-threaded portion 137 of the lead screw 134, the direction of rotation of the lead screw 134 can be reversed to move the second drive member 145 proximally relative to the first drive member 144 thereby rotating the knife 146 relative to the first drive member 144 to stow the knife into the longitudinal slot 108.

FIGS. 14A through 14E schematically illustrate another approach for articulating a knife in a surgical instrument 210, in accordance with many embodiments. The surgical instrument 210 includes a housing 212, a lead screw 134, a first drive member 214, a knife 216, a second drive member 218, a knife kick-up feature 220, and a knife kick-down feature 222. The housing 212 includes a proximal end 224, a distal end 226, an upper surface 228 extending between the proximal end 224 and the distal end 226, a proximal knife garage 230, a distal knife garage 232, a central cavity extending between the proximal end 224 and the distal end 226, and a longitudinal slot extending between the upper surface 228 and the central cavity. The lead screw 134 is mounted in the housing 212 for rotation relative to the housing 212 and extends between the proximal end 224 and the distal end 226 through the central cavity. The lead screw 134 has a threaded portion 135 and a non-threaded portion 137 disposed toward the distal end 226 relative to the threaded portion 135. The first and second drive members 214, 218 have internal threads configured to couple with the threaded portion 135 of the lead screw 134 for translation along the threaded portion 135 in response to rotation of the lead screw 134. The knife 216 is pivotally supported from the first drive member 214. The knife kick-up feature 220 and the knife kick-down feature 222 are coupled with the housing 212 and have fixed positions relative to the housing 212.

Figure 14A:
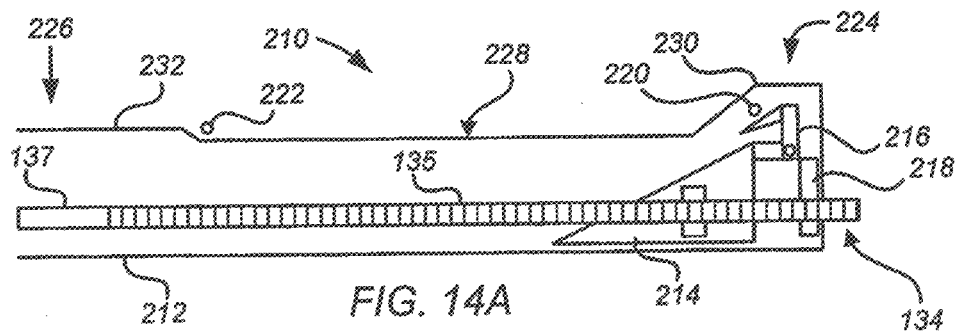
FIGS. 14A through 14E are schematic drawings illustrating articulation of a knife in a surgical instrument, in accordance with many embodiments.

FIG. 14A illustrates the surgical instrument 210 in a starting configuration in which the knife 216 is disposed in the proximal garage 230. The knife 216 is shown in a non-cutting orientation relative to the first drive member 214 (i.e., rotated relative to a cutting orientation of the knife shown in FIG. 14B). The non-cutting orientation of the knife may enable the use of a shorter housing by reducing the initial length of the combination of the first drive member 214 and the knife 216. A shorter housing provides for a more compact surgical instrument 210, thereby enhancing maneuverability of the surgical instrument and/or visibility within a surgical site. Alternatively, the knife member 216 can start in a cutting position.

From the starting configuration illustrated in FIG. 14A, rotation of the lead screw 134 simultaneously drives the first and second drive members 214, 218 distally along the lead screw 134. During the initial distal movement of the first drive member 214, the knife 216 contacts the kick-down feature 220, which causes rotation of the knife 216 relative to the first drive member 214 into the cutting position illustrated in FIG. 14B. In the cutting position, further rotation of the knife 216 relative to the first drive member 214 is blocked by the second drive member 218.

Figure 14B:
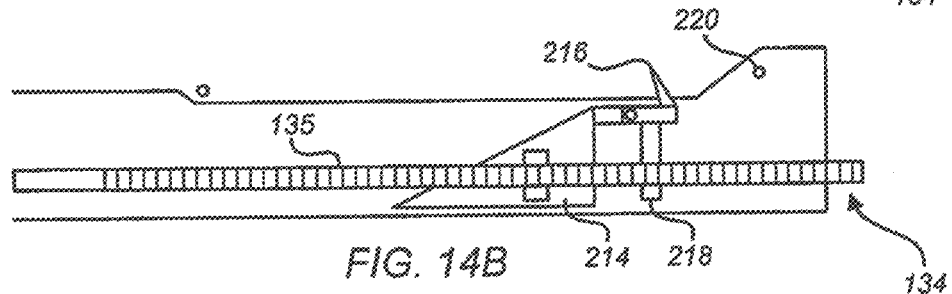
Figure 14C:
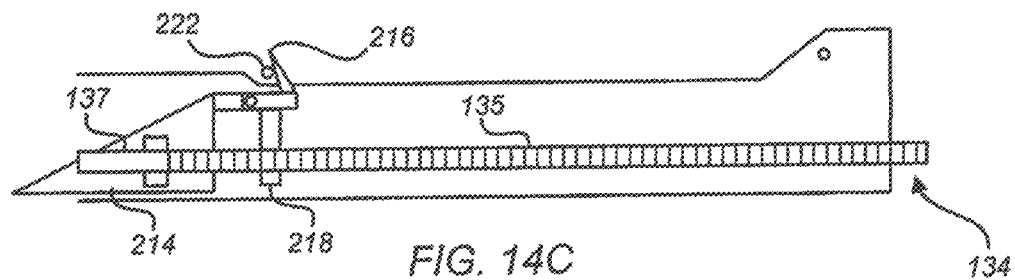
Figure 14D:
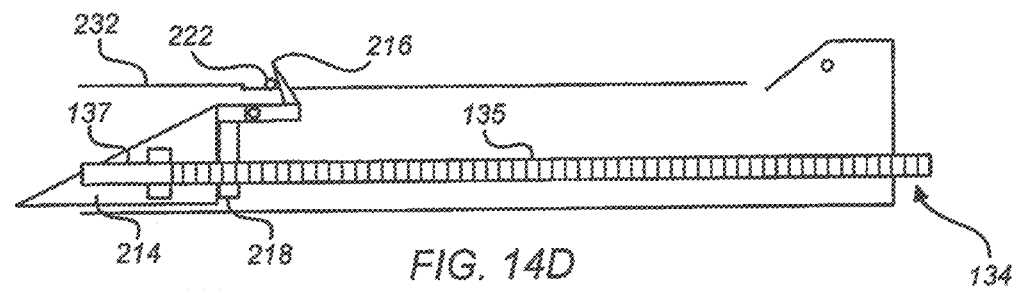
Figure 14E:
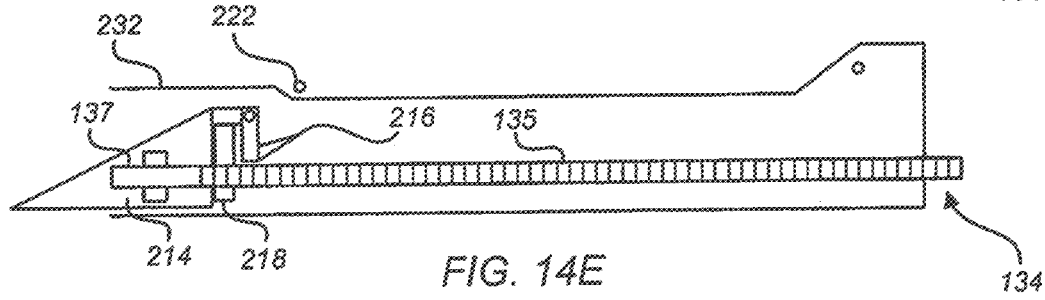

From the position shown in FIG. 14B, continued rotation of the lead screw 134 continues to simultaneously drive the first and second drive members 214, 218 distally along the lead screw 134 until the first drive member 214 is driven onto the non-threaded portion 137 of the lead screw 134 as illustrated in FIG. 14C. From the position illustrated in FIG. 14C, continued rotation of the lead screw 134 continues to drive only the second drive member 218 distally along the threaded portion 134 of the lead screw 134 to where the second drive member 218 contacts the first drive member 214 as illustrated in FIG. 14D. In the position illustrated in FIG. 14D, the second drive member 218 is no longer positioned to block rotation of the knife 216 relative to the first drive member 214. From the position illustrated in 14D, continued rotation of the lead screw 134 continues to drive the second drive member 218 along the threaded portion 135 of the lead screw 134, thereby also driving the first drive member 214 along the non-threaded portion 137 of the lead screw 134. By driving the first drive member 214 along the non-threaded portion 137 of the lead screw 134, the knife 216 contacts the kick-down feature 222, thereby ensuring that the knife 216 rotates down into the longitudinal slot for stowage into the distal knife garage 232 during the continued distal motion of the first and second drive members 214, 218 to the position illustrated in FIG. 14E.

Figure 15A:
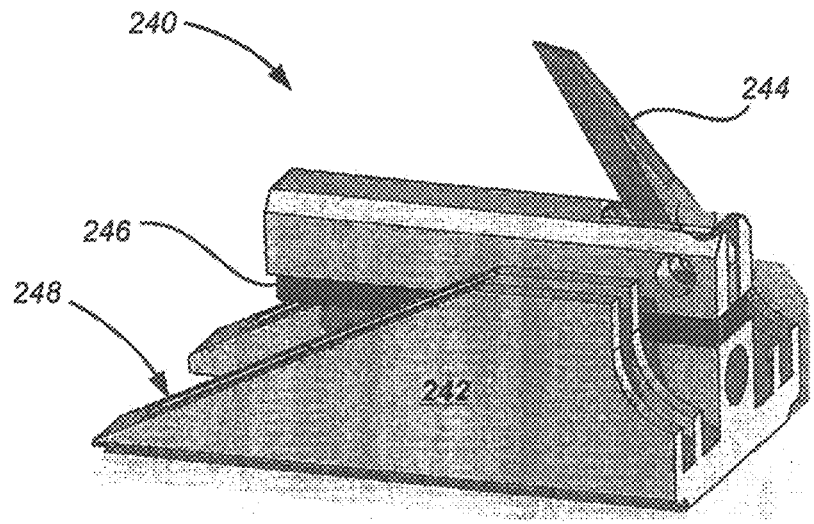
FIG. 15A is a perspective view illustrating knife articulation and staple deployment related components of a surgical instrument, in accordance with many embodiments.
Figure 15B:
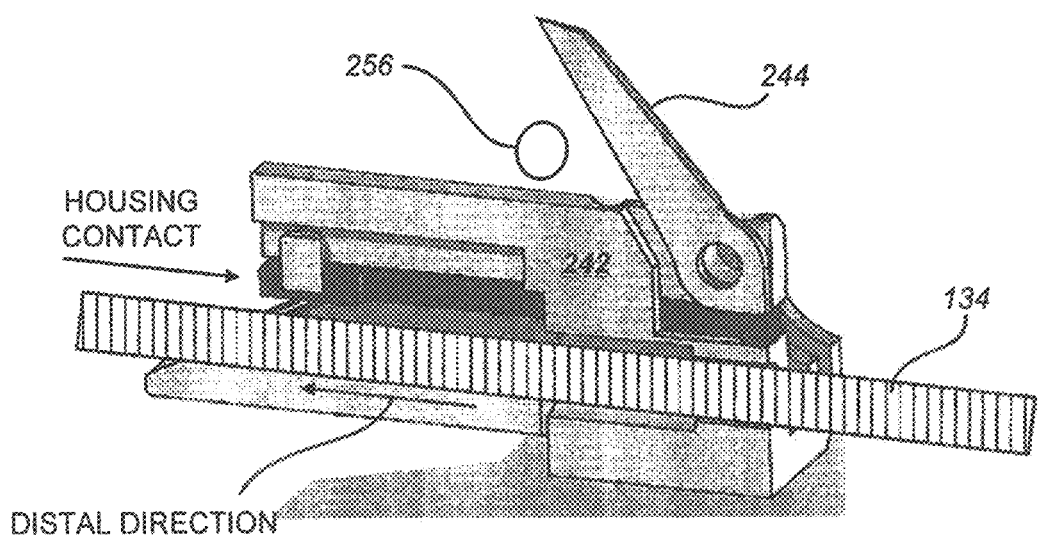
FIG. 15B is a perspective cross-sectional view illustrating a lead screw coupled with the components of FIG. 15A, in accordance with many embodiments.
Figure 15C:
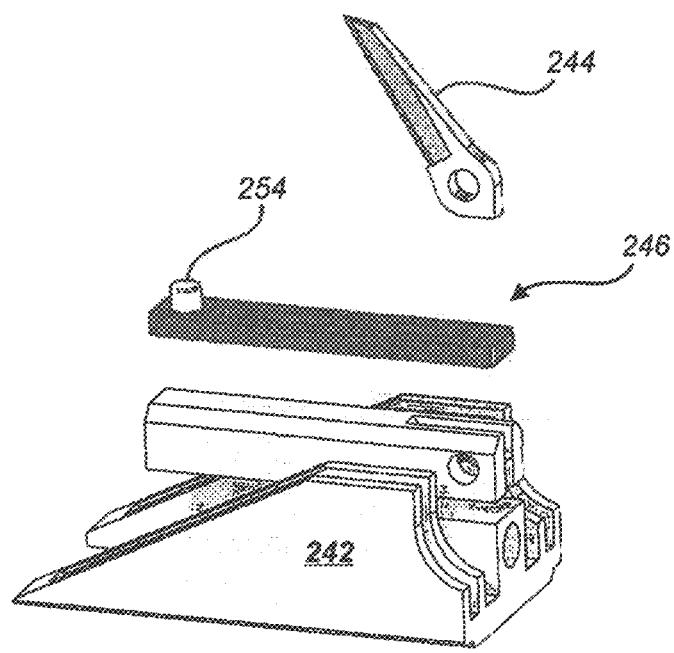
FIG. 15C is an exploded perspective view illustrating the components of FIG. 15A.
Figure 15D:
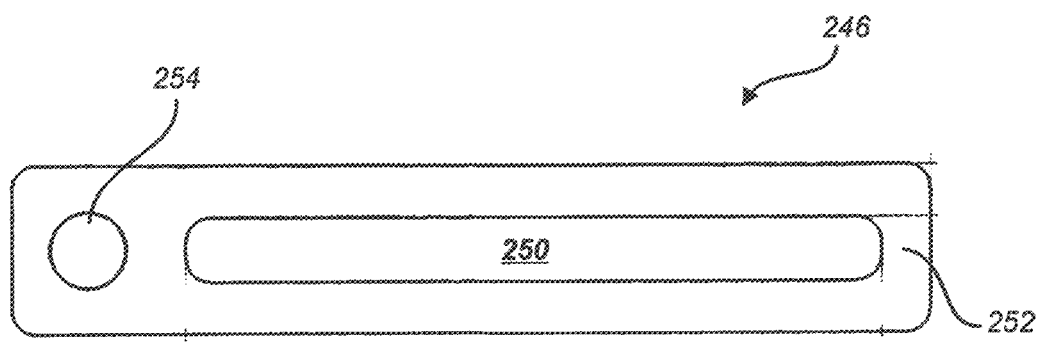
FIG. 15D is a plan view of a slidably mounted support element of the components of FIG. 15A.

FIGS. 15A through 15D illustrate another approach for articulating a knife in a surgical instrument, in accordance with many embodiments. A knife actuation assembly 240 includes a drive member 242, a knife 244, and a support member 246. The drive member 242 is internally threaded to operatively couple with a lead screw 134 for translation along the lead screw 134 in response to rotation of the lead screw 134. The drive member 242 includes distally facing ramps 248 configured to interface with staple pushers to deploy staples as the drive member 242 translates along the lead screw 134. The knife 244 is pivotally supported from the drive member 242 via a pivot pin (not shown). The support member 246 includes a central slot 250, a distal portion 252, and a guide pin 254. The support member 246 is slidably mounted in the drive member 242. The distal portion 252 of the support member 246 blocks a rotation of the knife 244 relative to the drive member 242 when the support member 246 is positioned relative to the drive member 242 as shown in FIGS. 15A and 15B.

The knife actuation assembly 240 is configured to maintain the configuration shown in FIGS. 15A and 15B from the start of articulation of the knife 244 to near the end of articulation of the knife 244, thereby maintaining the knife 244 in a cutting orientation relative to the drive member 242. For example, an interference fit between the support member 246 and the drive member 242 and/or a retaining provision (e.g., an adhesive, a frangible feature) can be used prevent inadvertent motion between the support member 246 and the drive member 242.

Near the end of the articulation of the knife 244, the support member 246 contacts a portion of the housing that prevents further distal movement of the support member 246 and does not prevent further distal movement of the drive member 242. Thereafter, continued rotation of the lead screw 134 produces further distal movement of the drive member 242 along the lead screw 134, thereby producing relative movement between the support member 246 and the drive member 242. The relative movement repositions the support member 246 to reposition the distal portion 252 and the central slot 250 of the support member 246 to permit the previously blocked rotation of the knife 244 relative to the drive member 242. Once the support member 246 has been repositioned relative to the drive member 242 to permit the previously blocked rotation of the knife 244 relative to the drive member 242, continued rotation of the lead screw 134 can be used to further move the drive member 242 distally along the lead screw 134 such that the knife 244 contacts a kick-down feature 256, which ensures rotation of the knife 244 relative to the drive member 242 to stow the knife 244.

Figure 16:
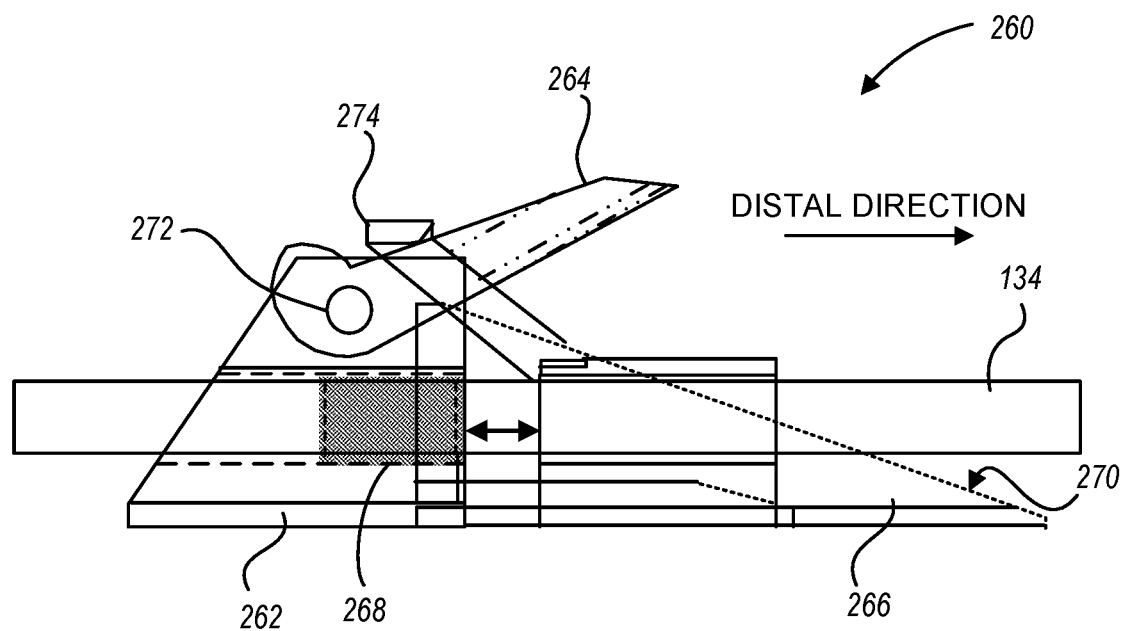
FIG. 16 is a side view illustrating knife articulation and staple deployment related components of a surgical instrument, in accordance with many embodiments.

FIG. 16 illustrates another approach for articulating a knife in a surgical instrument, in accordance with many embodiments. A knife actuation assembly 260 includes a drive member 262, a knife 264, a distal member 266, and a lead screw 134. The drive member 262 and the distal member 264 are slidably mounted in a housing and are mounted on the lead screw 134. The drive member 262 includes internal threads 268, which are operatively coupled with the lead screw 134 to move the drive member 262 along the lead screw 134 in response to rotation of the lead screw 134. The distal member 266 is not operatively coupled with the lead screw 134. Instead, the distal member 266 is pushed distally along the lead screw 134 by the drive member 262. The distal member 266 includes distal-facing ramp surfaces 270 configured to engage staple pushers as the distal member 266 is pushed along the lead screw 134 by the drive member 262. The knife 264 is pivotally supported from the drive member 262 via a pivot pin 272.

The assembly 260 is configured to orient the knife 264 in a cutting position when the drive member 262 pushes the distal member 264 along the lead screw and to stow the knife 264 when the drive member 262 is moved proximally relative to the distal member 264. The distal member 264 includes an interface feature 274 that interfaces with the knife 264 to rotationally orient the knife 264 relative to the drive member 262. When the drive member 262 is pushing the distal member 264, the interface feature 272 is positioned to orient the knife 264 in the cutting position and prevent rotation of the knife 264 about the pivot pin 272, thereby maintaining the knife 264 in the cutting position. The interface feature 272 also induces rotation of the knife 264 relative to the drive member 262 when the drive member 262 is moved proximally relative to the distal member 266, thereby stowing the knife 264. In operation, the lead screw 134 is first rotated to advance the drive member 262 distally along the lead screw 134 thereby pushing the distal member 266 along the lead screw 134 to deploy staples and to maintain the knife 264 in the cutting position. At the end of the distal movement of the assembly 260, the direction of rotation of the lead screw 134 is reversed to retract the drive member 262 proximally relative to the distal member 266, thereby causing the knife 264 to rotate down into the stowed position via interaction between the interface feature 272 and the knife 264.

Figure 17:
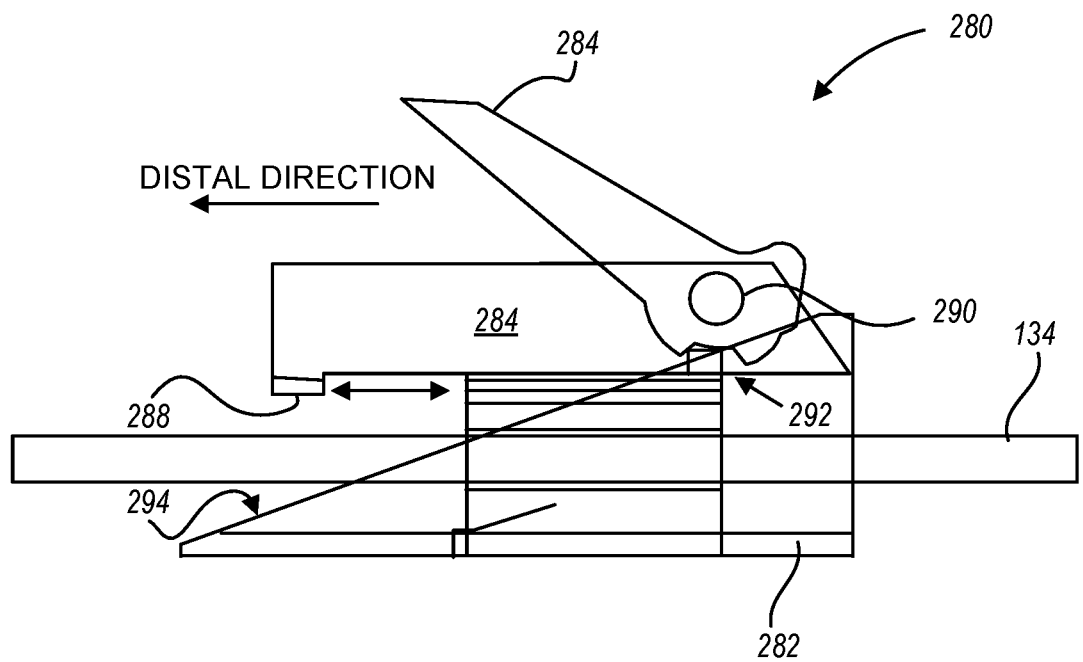
FIG. 17 is a side view illustrating knife articulation and staple deployment related components of a surgical instrument, in accordance with many embodiments.

FIG. 17 illustrates another approach for articulating a knife in a surgical instrument, in accordance with many embodiments. A knife actuation assembly 280 includes a drive member 282, a knife 284, a knife sled 286, and a lead screw 134. The drive member 282 and the knife sled 286 are slidably mounted in a housing. The drive member 282 includes internal threads operatively coupled with the lead screw 134 to move the drive member 282 along the lead screw 134 in response to rotation of the lead screw 134. The knife sled 286 is drivable distally by the drive member 282 via contact between the drive member 282 and a drive feature 288 of the knife sled 286. The knife 284 is pivotally supported from the knife sled 286 via a pivot pin 290. The angular orientation of the knife 284 relative to the knife sled 286 is coupled with the position of the drive member 282 relative to the knife sled 286 by an interface feature 292 of the drive member 282, which interfaces with the knife 284 to control the angular orientation of the knife 284 relative to the knife sled 286. The drive member 282 includes distal-facing ramp surfaces 294 configured to engage staple pushers as the drive member 282 moves distally along the lead screw 134.

The assembly 280 is configured to orient the knife 284 in a cutting position when the drive member 282 pushes the knife sled 286 along the lead screw 134 and to stow the knife 284 when the drive member 282 is moved proximally relative to the knife sled 286. In operation, the lead screw 134 is first rotated to advance the drive member 282 distally along the lead screw 134 thereby pushing the knife sled 286 in the distal direction and angularly orienting the knife 284 in the cutting position. At the end of the distal movement of the assembly 280, the direction of rotation of the lead screw 134 is reversed to retract the drive member 282 proximally relative to the knife sled 286, thereby causing the knife 284 to rotate down into the stowed position via interaction between the interface feature 292 and the knife 284.

Combinations and/or Modifications

The surgical instruments, assemblies, and cartridges disclosed herein can be modified and/or combined in any suitable fashion. For example, the cartridge 100 described herein can be modified to employ the knife articulation approach embodied in the surgical instrument 210 described herein, to employ the knife actuation assembly 240 as described herein, to employ the knife actuation assembly 260 as described herein, or to employ the knife actuation assembly 280 as described herein. Likewise, the surgical instrument 210 described herein can be modified to employ the knife actuation assembly 200 described herein, to employ the knife actuation assembly 240 as described herein, to employ the knife actuation assembly 260 as described herein, or to employ the knife actuation assembly 280 as described herein. And the surgical instruments, assemblies, and cartridges disclosed herein, or resulting from the foregoing modifications can be embodied in a detachably mountable cartridge such as cartridge 100 and can be embodied directly into a surgical instrument without being detachably mountable to an end effector of a surgical instrument.

Knife Articulation Methods

Figure 18:
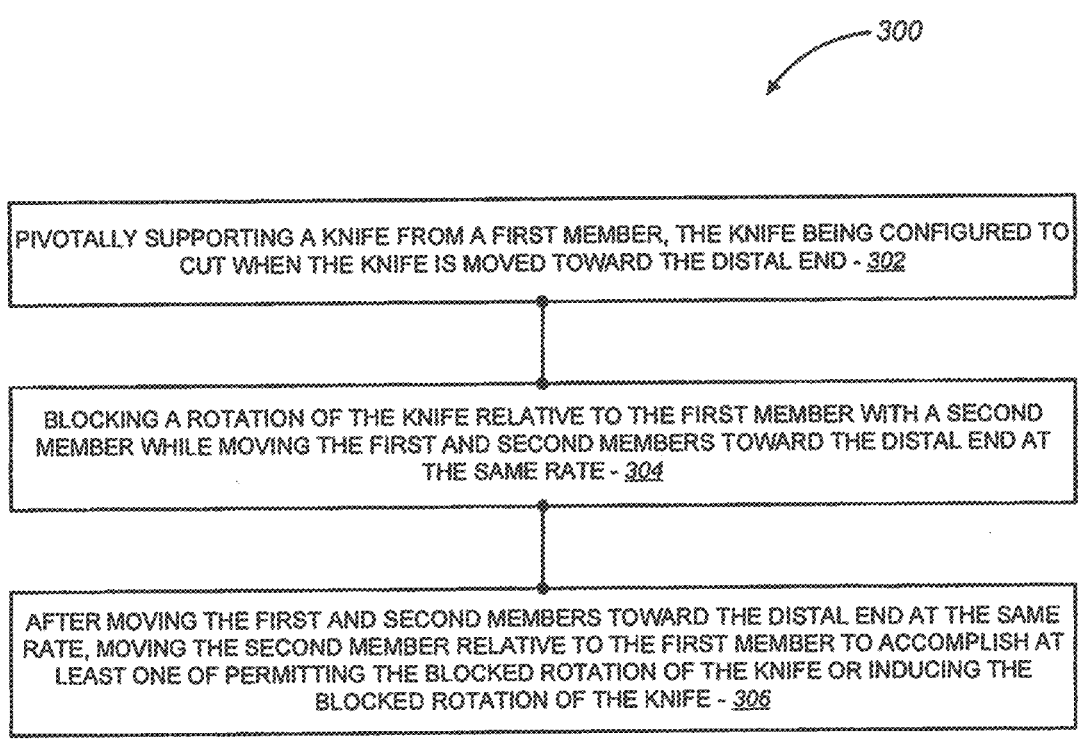
FIG. 18 lists acts of a method of articulating a cutting blade in a surgical instrument, in accordance with many embodiments.

FIG. 18 shows acts of a method 300 of articulating a knife in a surgical instrument, in accordance with many embodiments. Any suitable surgical instrument (e.g., stapling and cutting surgical instruments, electrosurgical vessel sealing devices) can be used to practice the method 300. For example, the linear stapling and cutting surgical instruments, cartridges, and related assemblies described herein can be used to practice the method 300.

In act 302, a knife is pivotally supported from a first member. The knife is configured to cut when the knife member is moved toward the housing distal end. In act 304, a rotation of the knife relative to the first member is blocked by a second member while moving the first and second members toward the distal end at the same rate. In act 306, after moving the first and second members toward the distal end at the same rate, the second member is moved relative to the first member to accomplish at least one of permitting the blocked rotation of the knife or inducing the blocked rotation of the knife.

Figure 19:
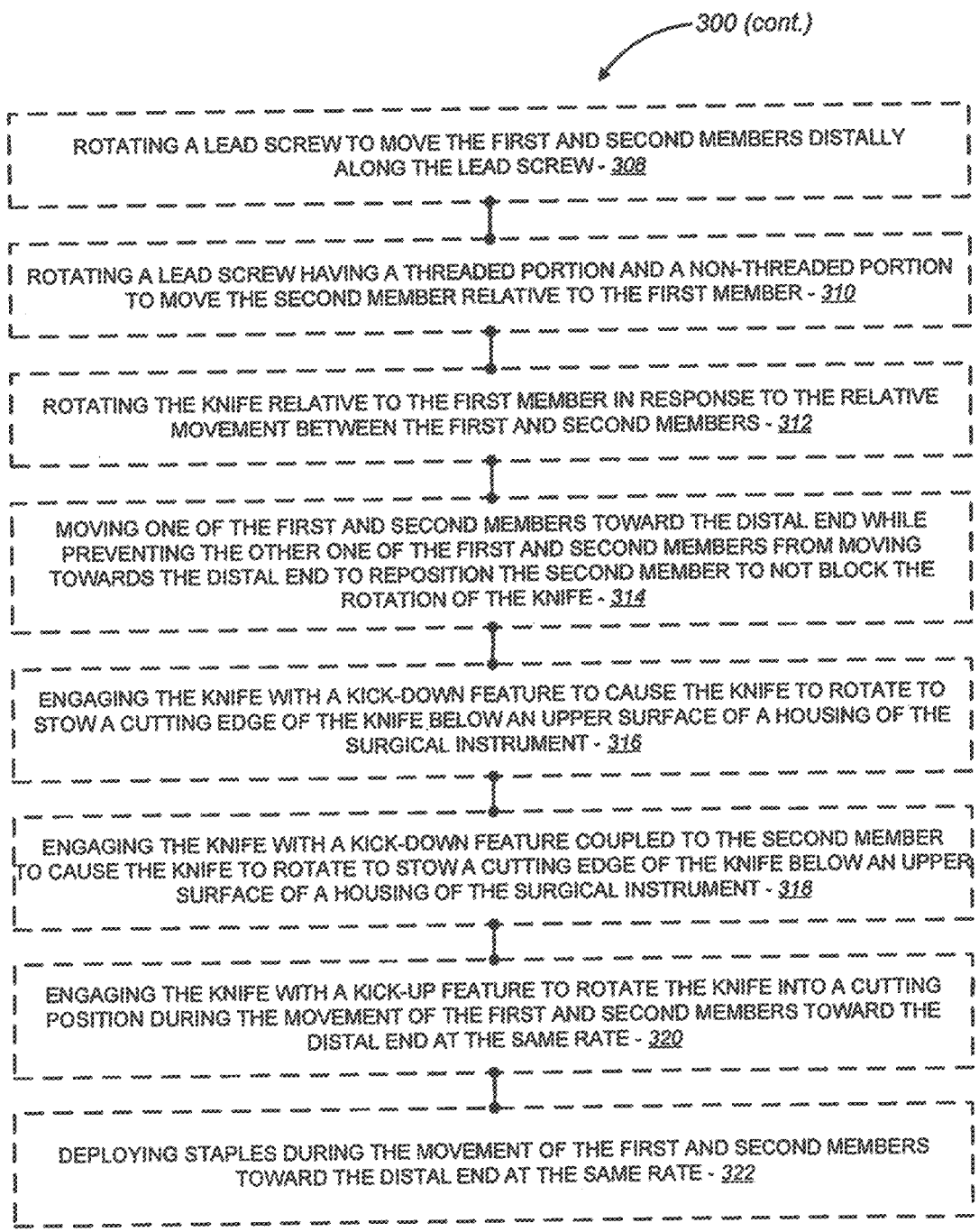
FIG. 19 lists optional acts of the method of FIG. 18.

FIG. 19 shows optional acts that can be accomplished in the method 300, in accordance with many embodiments. In optional act 308, a lead screw is rotated to move the first and second members distally along the lead screw. In optional act 310, a lead screw having a threaded portion and a non-threaded portion is rotated to move the second member relative to the first member. In optional act 312, the knife member is rotated relative to the first member in response to the relative movement between the first and second members. In optional act 314, one of the first and second members is moved toward the distal end while the other one of the first and second members is prevented from moving toward the distal end to reposition the second member to not block the rotation of the knife. In optional act 316, the knife is engaged with a kick-down feature to cause the knife to rotate to stow a cutting edge of the knife below an upper surface of a housing of the surgical instrument. In optional act 318, the knife is engaged with a kick-down feature coupled with the second member to cause the knife to rotate to stow a cutting edge of the knife below an upper surface of a housing of the surgical instrument. In optional act 320, the knife is engaged with a kick-up feature to rotate the knife into a cutting position during the movement of the first and second members toward the distal end at the same rate. In optional act 322, staples are deployed during the movement of the first and second members toward the distal end at the same rate.

The methods disclosed herein can be employed in any suitable application. For example, the methods disclosed herein can be employed in surgical instruments, manual or powered, hand-held or robotic, directly controlled or tele-operated, for open or minimally invasive (single or multi-port) procedures.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical instrument comprising:
   an elongated shaft having a shaft distal end; and
   an end effector coupled to the shaft distal end, the end effector having a first end and a second end, the end effector including:
   a first member movable towards the second end of the end effector;
   a knife member pivotally coupled to the first member;
   a second member movable towards the second end of the end effector; and
   a lead screw that extends through at least one of the first member and the second member, wherein the lead screw is operatively coupled with at least one of the first member and the second member to generate a translation of the first member and the second member towards the second end of the end effector,
   wherein the knife member is configured to be in a cutting position during the translation of the first member and the second member towards the second end of the end effector, and
   wherein the knife member is rotatable relative to the first member to stow the knife member into a non-cutting position after the translation of the first member and the second member towards the second end of the end effector.

2. The surgical instrument of claim 1, wherein the end effector further comprises:
two opposed jaws and
a housing included in one of the two opposed jaws, the housing including a housing proximal end, a housing distal end, an upper surface extending between the housing proximal end and the housing distal end, a central cavity extending between the housing proximal end and the housing distal end, and a longitudinal slot extending through the upper surface,
wherein the first member and the second member are configured to simultaneously translate through the central cavity towards the housing distal end.

3. The surgical instrument of claim 2, wherein:
the knife member is rotatable relative to the first member to stow the knife member into the longitudinal slot after the translation of the first member and the second member through the central cavity towards the housing distal end.

4. The surgical instrument of claim 2, wherein:
the second member blocks rotation of the knife member during the translation of the first member and the second member through the central cavity towards the housing distal end to maintain the knife member in the cutting position; and
the second member contacts a portion of the housing that prevents further movement of the second member towards the second end of the end effector during a further movement of the first member so as to reposition the second member relative to the first member to permit rotation of the knife member relative to the first member for stowing the knife member into the longitudinal slot.

5. The surgical instrument of claim 2, wherein:
the end effector includes staple openings and staples disposed in the staple openings; and
each of the staples is deployed during the translation of the first member and the second member through the central cavity towards the housing distal end.

6. The surgical instrument of claim 2, wherein the lead screw is operatively coupled with each of the first member and the second member to generate the translation of the first member and the second member through the central cavity towards the housing distal end.

7. The surgical instrument of claim 6, wherein:
the lead screw has a threaded portion and a non-threaded portion disposed distally of the threaded portion;
each of the first member and the second member is driven along the lead screw during the translation of the first member and the second member through the central cavity towards the housing distal end; and
one of the first member and the second member interfaces with the non-threaded portion and the other one of the first member and the second member interfaces with the threaded portion to generate relative movement between the first member and the second member after the translation of the first member and the second member through the central cavity towards the housing distal end.

8. The surgical instrument of claim 1, wherein the end effector further comprises:
two opposed jaws and
a housing included in one of the two opposed jaws, the housing including a housing proximal end, a housing distal end, and an upper surface extending between the housing proximal end and the housing distal end,
wherein the first member and the second member are configured to translate towards the housing distal end,
wherein in the cutting position, a cutting edge of the knife member extends above the housing upper surface during the translation of the first member and the second member towards the housing distal end, and
wherein the knife member is configured to be rotated relative to the first member to stow the cutting edge of the knife member below the housing upper surface after the translation of the first member and the second member towards the housing distal end.

9. The surgical instrument of claim 1, wherein the knife member includes gear teeth that mate with gear teeth coupled with the second member so that relative movement between the first member and the second member causes rotation of the knife member relative to the first member to stow the knife member into the non-cutting position.

10. A surgical instrument comprising:
an elongated shaft having a shaft distal end; and
an end effector coupled to the shaft distal end, the end effector having a first end and a second end, the end effector including:
a first member movable towards the second end of the end effector;
a knife member pivotally coupled to the first member;
a second member movable towards the second end of the end effector;
two opposed jaws;
a housing included in one of the two opposed jaws, the housing including a housing proximal end, a housing distal end, an upper surface extending between the housing proximal end and the housing distal end, a central cavity extending between the housing proximal end and the housing distal end, and a longitudinal slot extending through the upper surface; and
a kick-up feature coupled with the housing to rotate the knife member relative to the first member into a cutting position during a translation of the first member and the second member through the central cavity towards the housing distal end,
wherein the knife member is configured to be in a cutting position during the translation of the first member and the second member towards the second end of the end effector, and
wherein the knife member is rotatable relative to the first member to stow the knife member into a non-cutting position after the translation of the first member and the second member towards the second end of the end effector.

11. A surgical instrument comprising:
an elongated shaft having a shaft distal end; and
an end effector coupled to the shaft distal end, the end effector having a first end and a second end, the end effector including:
a first member movable towards the second end of the end effector;
a knife member pivotally coupled to the first member;
a second member movable towards the second end of the end effector;
two opposed jaws;
a housing included in one of the two opposed jaws, the housing including a housing proximal end, a housing distal end, an upper surface extending between the housing proximal end and the housing distal end, a central cavity extending between the housing proximal end and the housing distal end, and a longitudinal slot extending through the upper surface; and a kick-down feature coupled with the housing to rotate the knife member relative to the first member to stow the knife member into the longitudinal slot,
wherein the knife member is configured to be in a cutting position during a translation of the first member and the second member towards the second end of the end effector, and
wherein the knife member is rotatable relative to the first member to stow the knife member into a non-cutting position after the translation of the first member and the second member towards the second end of the end effector.

12. A demountably attachable cartridge of a surgical instrument, the cartridge having a first end and a second end, the cartridge comprising:
a first member movable towards the second end of the cartridge;
a knife member pivotally coupled to the first member;
a second member movable towards the second end of the cartridge; and
a leadscrew that extends through at least one of the first member and the second member, wherein the leadscrew is operatively coupled with at least one of the first member and the second member to generate a translation of the first member and the second member towards the second end of the cartridge,
wherein the knife member is configured to be in a cutting position during the translation of the first member and the second member towards the second end of the cartridge, and
wherein the knife member is rotatable relative to the first member to stow the knife member into a non-cutting position after the translation of the first member and the second member towards the second end of the cartridge.

13. The cartridge of claim 12, further comprising a housing having a housing proximal end, a housing distal end, an upper surface extending between the housing proximal and distal ends, a central cavity extending between the housing proximal and distal ends, and a longitudinal slot extending through the upper surface, wherein the first member and the second member are configured to simultaneously translate through the central cavity towards the housing distal end.

14. The cartridge of claim 13, wherein:
the knife member is rotatable relative to the first member to stow the knife member into the longitudinal slot after the translation of the first member and the second member through the central cavity towards the housing distal end.

15. The cartridge of claim 13, wherein:
the second member blocks rotation of the knife member during the translation of the first member and the second member through the central cavity towards the housing distal end to maintain the knife member in the cutting position; and
the second member contacts a portion of the housing that prevents further movement of the second member towards the second end of the cartridge during a further movement of the first member so as to reposition the second member relative to the first member to permit rotation of the knife member relative to the first member for stowing the knife member into the longitudinal slot.

16. The cartridge of claim 13, wherein the lead screw is operatively coupled with each of the first member and the second member to generate the translation of the first member and the second member through the central cavity towards the housing distal end.

17. The cartridge of claim 16, wherein:
the lead screw has a threaded portion and a non-threaded portion disposed distally of the threaded portion;
each of the first member and the second member is driven along the lead screw during the translation of the first member and the second member through the central cavity towards the housing distal end; and
one of the first member and the second member interfaces with the non-threaded portion and the other one of the first member and the second member interfaces with the threaded portion to generate relative movement between the first member and the second member after the translation of the first member and the second member through the central cavity towards the housing distal end.

18. The cartridge of claim 12, wherein the knife member includes gear teeth that mate with gear teeth coupled with the second member so that relative movement between the first member and the second member causes rotation of the knife member relative to the first member to stow the knife member into the non-cutting position.

19. The cartridge of claim 12, further comprising:
a housing having a housing proximal end, a housing distal end, and an upper surface extending between the housing proximal and distal ends,
wherein the first member and the second member are configured to translate towards the housing distal end,
wherein in the cutting position, a cutting edge of the knife member extends above the housing upper surface during the translation of the first member and the second member towards the housing distal end, and
wherein the knife member is configured to be rotated relative to the first member to stow the cutting edge of the knife member below the housing upper surface after the translation of the first member and the second member towards the housing distal end.

20. A demountably attachable cartridge of a surgical instrument, the cartridge having a first end and a second end, the cartridge comprising:
a first member movable towards the second end of the cartridge;
a knife member pivotally coupled to the first member;
a second member movable towards the second end of the cartridge;
two opposed jaws;
a housing included in one of the two opposed jaws, the housing including a housing proximal end, a housing distal end, an upper surface extending between the housing proximal and distal ends, a central cavity extending between the housing proximal and distal ends, and a longitudinal slot extending through the upper surface; and
a kick-up feature coupled with the housing to rotate the knife member relative to the first member into a cutting position during a translation of the first member and the second member through the central cavity towards the housing distal end,
wherein the knife member is configured to be in a cutting position during the translation of the first member and the second member towards the second end of the cartridge, and
wherein the knife member is rotatable relative to the first member to stow the knife member into a non-cutting position after the translation of the first member and the second member towards the second end of the cartridge.

21. A demountably attachable cartridge of a surgical instrument, the cartridge having a first end and a second end, the cartridge comprising:
- a first member movable towards the second end of the cartridge;
- a knife member pivotally coupled to the first member;
- a second member movable towards the second end of the cartridge;
- two opposed jaws;
- a housing included in one of the two opposed jaws, the housing including a housing proximal end, a housing distal end, an upper surface extending between the housing proximal and distal ends, a central cavity extending between the housing proximal and distal ends, and a longitudinal slot extending through the upper surface; and
- a kick-down feature coupled with the housing to rotate the knife member relative to the first member to stow the knife member into the longitudinal slot,
- wherein the knife member is configured to be in a cutting position during a translation of the first member and the second member towards the second end of the cartridge, and
- wherein the knife member is rotatable relative to the first member to stow the knife member into a non-cutting position after the translation of the first member and the second member towards the second end of the cartridge.

* * * * *